(12) United States Patent
White et al.

(10) Patent No.: US 8,900,240 B2
(45) Date of Patent: Dec. 2, 2014

(54) SPINAL ROD AND SCREW SECURING APPARATUS AND METHOD

(75) Inventors: John White, Marquette, MI (US);
Daniel Rae Robinson, Marquette, MI (US); Matthew F. Hanfelt, Marquette, MI (US); Jason P. Sandstrom, Marquette, MI (US); Jeffrey A. Hoffman, Anchorage, AK (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 628 days.

(21) Appl. No.: 13/025,715

(22) Filed: Feb. 11, 2011

(65) Prior Publication Data

US 2011/0202096 A1 Aug. 18, 2011

Related U.S. Application Data

(60) Provisional application No. 61/304,123, filed on Feb. 12, 2010.

(51) Int. Cl.
*A61B 17/70* (2006.01)
*A61B 17/86* (2006.01)

(52) U.S. Cl.
CPC ......... *A61B 17/7032* (2013.01); *A61B 17/8605* (2013.01); *A61B 17/8685* (2013.01); *A61B 17/864* (2013.01); *A61B 17/7086* (2013.01)
USPC ...................................... 606/86 A

(58) Field of Classification Search
USPC .............. 606/86 R, 86 A, 916, 246–279
See application file for complete search history.

(56) References Cited

U.S. PATENT DOCUMENTS

| 1,359,164 | A | 11/1920 | Giudice et al. |
|---|---|---|---|
| 1,832,879 | A | 11/1931 | Ruskin |
| 1,863,037 | A | 6/1932 | Archbold |
| 1,985,108 | A | 12/1934 | Rush |
| 1,977,282 | A | 10/1935 | Kruse |
| 2,370,308 | A | 2/1945 | Hanson |
| 2,523,385 | A | 9/1950 | Mead |

(Continued)

FOREIGN PATENT DOCUMENTS

| WO | 9311715 | 6/1993 |
|---|---|---|
| WO | 2006019641 | 2/2006 |
| WO | 2006047659 | 5/2006 |

OTHER PUBLICATIONS

Brochure, "Spiral Radium 90D.TM. Surgical Technique," Tyco Healthcare/Surgical Dynamics, 11 pages.

(Continued)

*Primary Examiner* — Mary Hoffman
*Assistant Examiner* — Michelle C Eckman
(74) *Attorney, Agent, or Firm* — Fitch, Even, Tabin & Flannery LLP

(57) ABSTRACT

A minimally invasive and open surgery surgical system for implanting spinal screw assemblies to be connected by a spinal rod is disclosed. In one form, the system includes an improved tool device for inserting a cap insert into an initial and final locking of a screw assembly and securing a spinal rod inserted through an incision to a vertebra. In another form, the system also includes a screw fixation system that allows greater variability in thread diameter for orthopedic implant for in the spine, iliac crest, or bones.

13 Claims, 35 Drawing Sheets

(56) References Cited

U.S. PATENT DOCUMENTS

| | | |
|---|---|---|
| 2,594,102 A | 4/1952 | Vollmer |
| 2,598,650 A | 5/1952 | Smith et al. |
| 2,655,953 A | 10/1953 | Milochei |
| 2,664,774 A | 1/1954 | Harvie |
| 2,669,145 A | 2/1954 | Mead |
| 2,814,222 A | 11/1957 | Sanders |
| 3,181,181 A | 5/1965 | Buckley et al. |
| 3,477,429 A | 11/1969 | Sampson |
| 3,486,505 A | 12/1969 | Morrison |
| 3,618,612 A | 11/1971 | Ahn |
| 3,641,652 A | 2/1972 | Arnold et al. |
| 3,981,308 A | 9/1976 | Schlein |
| 4,050,464 A | 9/1977 | Hall |
| 4,111,206 A | 9/1978 | Vishnevsky et al. |
| 4,147,167 A | 4/1979 | Hickmann et al. |
| 4,153,321 A | 5/1979 | Pombrol |
| 4,271,836 A | 6/1981 | Bacal et al. |
| 4,316,468 A | 2/1982 | Klieman et al. |
| 4,318,316 A | 3/1982 | Guilliams |
| 4,325,376 A | 4/1982 | Klieman et al. |
| 4,409,968 A | 10/1983 | Drummond |
| 4,411,259 A | 10/1983 | Drummond |
| 4,445,513 A | 5/1984 | Ulrich et al. |
| D291,729 S | 9/1987 | Greig |
| 4,793,225 A | 12/1988 | Berkich |
| 4,809,695 A | 3/1989 | Gwathmey et al. |
| 4,870,965 A | 10/1989 | Jahanger |
| 4,896,661 A | 1/1990 | Bogert et al. |
| 4,898,161 A | 2/1990 | Grundei |
| 4,911,154 A | 3/1990 | Vickers |
| 4,927,425 A | 5/1990 | Lozier |
| 4,950,273 A | 8/1990 | Briggs |
| 4,966,600 A | 10/1990 | Songer et al. |
| 5,020,519 A | 6/1991 | Hayes et al. |
| D331,625 S | 12/1992 | Price et al. |
| 5,167,662 A | 12/1992 | Hayes et al. |
| D346,217 S | 4/1994 | Sparker et al. |
| 5,364,397 A | 11/1994 | Hayes et al. |
| 5,368,596 A | 11/1994 | Burkhart |
| 5,466,243 A * | 11/1995 | Schmieding et al. .......... 606/232 |
| 5,616,143 A | 4/1997 | Schlapfer et al. |
| 5,704,937 A | 1/1998 | Martin |
| 5,720,751 A | 2/1998 | Jackson |
| 5,782,831 A | 7/1998 | Sherman et al. |
| 5,885,299 A | 3/1999 | Winslow et al. |
| 5,899,901 A | 5/1999 | Middleton |
| 5,910,141 A | 6/1999 | Morrison et al. |
| 5,951,564 A | 9/1999 | Schroder et al. |
| 6,017,342 A | 1/2000 | Rinner |
| 6,036,692 A | 3/2000 | Burel et al. |
| 6,063,088 A | 5/2000 | Winslow |
| 6,083,225 A | 7/2000 | Winslow et al. |
| 6,139,549 A | 10/2000 | Keller |
| 6,251,111 B1 | 6/2001 | Barker et al. |
| 6,261,296 B1 | 7/2001 | Aebi et al. |
| 6,440,133 B1 | 8/2002 | Beale et al. |
| 6,478,801 B1 | 11/2002 | Ralph et al. |
| 6,565,570 B2 | 5/2003 | Sterett et al. |
| 6,648,888 B1 | 11/2003 | Shluzas |
| 6,660,006 B2 | 12/2003 | Markworth et al. |
| 6,676,665 B2 | 1/2004 | Foley et al. |
| 6,689,140 B2 | 2/2004 | Cohen |
| 6,716,218 B2 | 4/2004 | Holmes et al. |
| 6,746,449 B2 | 6/2004 | Jones et al. |
| 6,790,208 B2 | 9/2004 | Oribe et al. |
| 6,790,209 B2 | 9/2004 | Beale et al. |
| 7,141,051 B2 | 11/2006 | Janowski et al. |
| 7,278,995 B2 | 10/2007 | Nichols et al. |
| 7,763,049 B2 | 7/2010 | Roychowdhury |
| 7,771,430 B2 | 8/2010 | Jones et al. |
| 7,776,040 B2 | 8/2010 | Markworth et al. |
| 7,828,829 B2 | 11/2010 | Ensign |
| 7,887,539 B2 | 2/2011 | Dunbar, Jr. et al. |
| 7,922,724 B2 * | 4/2011 | Lim ........................ 606/86 A |
| 7,931,654 B2 | 4/2011 | Jones et al. |
| 8,192,439 B2 | 6/2012 | Songer et al. |
| 8,308,774 B2 * | 11/2012 | Hoffman et al. ............. 606/279 |
| 8,545,505 B2 | 10/2013 | Sandstrom et al. |
| 2004/0049191 A1 * | 3/2004 | Markworth et al. ........... 606/61 |
| 2004/0220573 A1 * | 11/2004 | McDevitt et al. .............. 606/72 |
| 2006/0025768 A1 | 2/2006 | Lott et al. |
| 2006/0089651 A1 | 4/2006 | Trudeau et al. |
| 2006/0129149 A1 | 6/2006 | Iott et al. |
| 2008/0039839 A1 * | 2/2008 | Songer et al. .................. 606/61 |
| 2008/0154277 A1 | 6/2008 | Machalk et al. |
| 2009/0228054 A1 * | 9/2009 | Hoffman et al. ............ 606/86 A |

OTHER PUBLICATIONS

Brochure, "Universal Instrumentation (CD) for Spinal Surgery," Dr. Cotrel et al., Stuart, 1985, 20 pages.

U.S. Appl. No. 60/784,674, filed Mar. 22, 2006, entitled Low Top Pedicle Screw, 4 pages.

U.S. Appl. No. 60/981,821, filed Oct. 23, 2007, entitled Low Top Bone Fixation System and Method for Using the Same, 64 pages.

U.S. Appl. No. 60/901,157, filed Feb. 14, 2007, entitled Low Top Spondy Reducer and Provisional Locker, 6 pages.

* cited by examiner

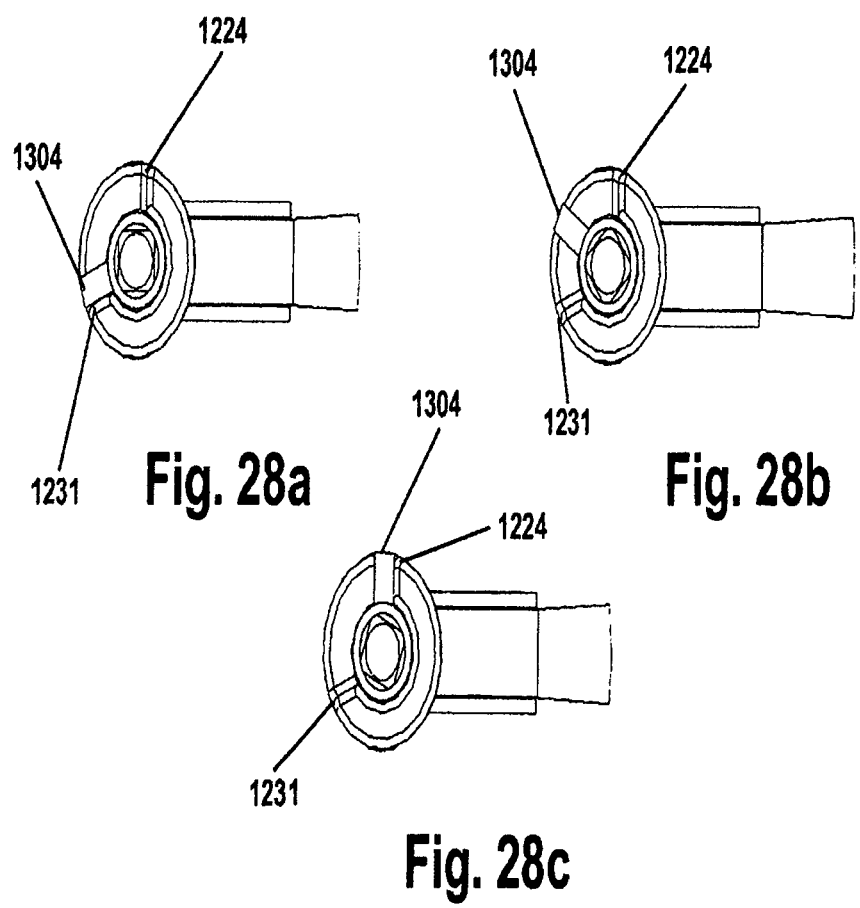

SPINAL ROD AND SCREW SECURING APPARATUS AND METHOD

CROSS REFERENCE TO RELATED APPLICATION

This patent claims benefit under 35 U.S.C. §119 (e) to U.S. Provisional Application No. 61/304,123 entitled "Spinal Rod and Screw Securing Apparatus and Method" filed Feb. 12, 2010, the contents of which are incorporated herein by reference in its entirety.

INCORPORATION BY REFERENCE

U.S. Utility application Ser. No. 11/844,259, filed Aug. 23, 2007 and entitled MINIMALLY INVASIVE SURGICAL SYSTEM, is incorporated by reference as if reproduced in its entirety, herein.

FIELD OF THE INVENTION

The device disclosed herein provides an instrument for manipulating and securing bone fixation systems for the promotion of proper bone alignment and fusion, in particular, spinal fusion. In the preferred embodiment, the drive tool apparatus is similar to the class of medical instruments generally referred to as rod persuaders, spinal rod reducers and pedicle screw cap inserters, but is not limited to that class of devices.

The invention also relates generally to an apparatus and method for surgically implanting a fixation device, more particularly, to an apparatus and surgical method that secures bone or bone segments relative to one another with minimal invasion into the surrounding body tissue. Conversely the present invention is also compatible with conventional "open" surgical approaches for the treatment of more serious trauma injuries, or diseases such as scoliosis.

BACKGROUND OF THE INVENTION

Implant devices secured to bone or bone segments are utilized to promote the healing and repair of various parts of the human body. In some cases, the implant devices are secured to bone or bone segments such that the bones themselves heal, fuse, or stabilize relative to one another. In other cases, implant or fixation devices are used to secure bones or bone fragments such that the surrounding soft tissue may heal without being disturbed by relative movement of the bones.

During the surgical procedure to implant fixation devices, a plurality of bone screws or other fixation elements, in concert with coupling members, are secured to a plurality of respective bones. Each of the bone screws, or anchor members, is then secured relative to the others with an additional apparatus, such as a connecting member, brace or rod. A pedicle screw and rod system is one such example that is commonly used to secure adjacent vertebrae together in a desired relationship.

As an example, a patient may require that a number of vertebrae be secured so that fusion of the bones may take place. To accomplish fusion a number of bone anchors may be secured to a plurality of vertebrae via threaded engagement or by hooks that engage anatomy about the vertebrae. Each bone anchor or hook may be integrally attached to a coupling member which often include upstanding walls forming a u-shape resembling a yoke. The coupling members may be integral with the anchor member head or may be movably attached and articulate relative to the anchor members. Each coupling member in turn may be secured relative to the other coupling members by a connecting member or rod. A locking device or cap is driven into each of the coupling members ultimately locking the rod relative to each coupling member.

When positioning a bone anchor or hook, the orientation of the anatomical structures often results in a skewed relationship of the coupling members relative to each other. The connecting member, once placed in the coupling members, is utilized to reorient the vertebrae in a more desirable relationship. Undesirable relationships of vertebrae are often attributed to disc collapse, trauma, or disease such as scoliosis. In the case of collapse, distraction of the vertebrae may be desirable. If the anchor, coupling member and rod accompany an interbody device, contraction of the vertebrae to promote fusion may be desirable. However in the case of trauma or scoliosis, the connecting member may be pre-bent in a predetermined manner conforming to the ultimate desired position of the vertebrae. The deformation, or bend, of the spinal connecting member takes the shape of the desired spinal alignment and thus will likely not conform to the skewed relationship of the coupling members. The connecting member or rod may need to be reduced and or rotated to be captured in the coupling members.

The reduction and rotation of spinal rods is currently accomplished by devices relying on threaded mechanisms for linear advancement of the rods into the coupling members. While these devices may be effective, they are typically complicated, bulky, involve many revolutions to achieve reduction, offer little in the way of tactile feed back to the operator, require two hands for the reduction process, and are not easily adapted to minimally invasive surgery.

Minimally invasive surgeries require that only small incisions be made (typically ¾") in the skin of the patient posterior to each vertebrae requiring a spinal implant assembly. Tissues that impede entry to the surgical site are then distracted, and a pedicle screw assembly, typically attached to an anchor extension or yoke manipulator, is introduced to the surgical site. All subsequent procedures take place in or adjacent to the yoke manipulator including, but not limited to, rod reduction, rod rotation, and deployment and securance of a locking device. Typical instruments that perform rod reduction are not adaptable from open surgery techniques to the limited area afforded in minimally invasive surgery. In addition the complexity of current instruments, their method of operation, and the need for additional tools to complete the surgery lead to lengthier surgical times.

SUMMARY OF THE INVENTION

For these reasons it is desirable to have an improved drive tool apparatus that can be utilized in both minimally invasive and open spinal surgery that provides ease of rod reduction and rotation while decreasing the time of surgery. In addition, the instrument should provide the operator a simple stationary grip to apply anti torque while other instruments within the tool are rotated. The instrument should allow for both the initial and final locking of a cap in a coupling member thus reducing the number of additional instruments necessary to successfully complete a spinal reduction surgery.

A drive tool apparatus is provided for securing a locking device and a connecting element within a coupling member anchored to a vertebral body. The apparatus has an attachment mechanism for quick engagement to an anchor extension and a single actuating lever that is operable to advance a drive rod, releasably attached to a locking device, linearly along the longitudinal axis of the drive tool. In addition the drive rod of the apparatus is rotatable to initially capture a locking device and connecting element in a coupling member and ultimately fully securing the locking device or cap within the coupling member thus fixing all elements relative to one another. The act of squeezing the lever and advancing the drive rod provides the operator with immediate and constant tactile feedback as to the forces the drive tool is encountering. The stop mechanism insures that the drive rod can only travel in a distal direction, thus the operator need not be concerned with sudden or rapid movement of the drive rod in a proximal direction when releasing the actuating lever. The mechanical guide on the drive tool provides the operator with visual feedback as to the orientation of the locking device and to the depth to which the drive tool has advanced. The mechanical guide thus eliminates the need for the surgeon to determine or guess when the drive rod is fully linearly advanced. The two walls on the mechanical guide give the operator a visual aid during rotation of the drive rod indicating the current status as to whether the locking device is temporarily locked or fully locked. In the fully locked position, the drive rod is no longer mechanically engaged with the drive tool and thus can be easily removed.

BRIEF DESCRIPTION OF THE DRAWINGS

FIG. 28a is a top view of the alignment pin of the drive rod abutting the zero degree wall of the mechanical guide on the drive tool;

FIG. 28b is a top view of the alignment pin of the drive rod in the 40-50 degree position on the mechanical guide on the drive tool indicating temporary lock;

FIG. 28c is a top view of the alignment pin of the drive rod abutting the hard stop wall of the mechanical guide on the drive tool indicating fully locked;

DETAILED DESCRIPTION OF THE PREFERRED EMBODIMENTS

Figure 1:
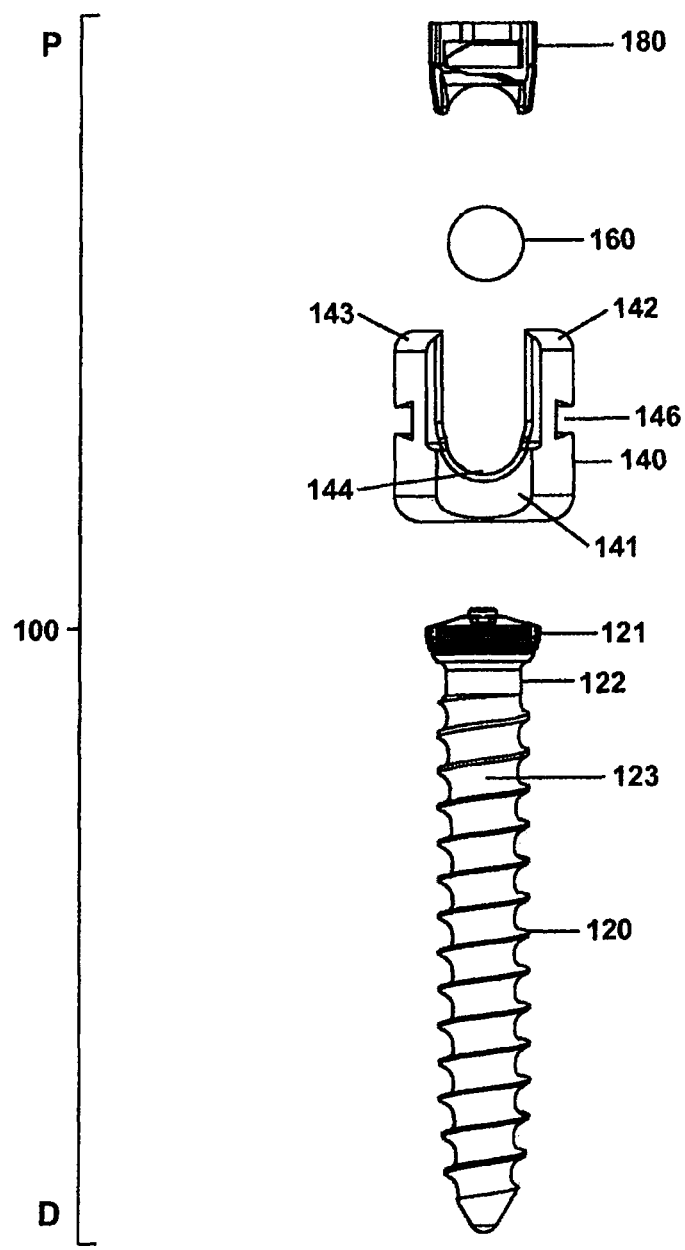
FIG. 1 illustrates an exploded front view of a pedicle screw assembly.

Prior rod persuader designs typically rely on threaded drive systems, such as in U.S. Pat. No. 7,278,995 to Nichols et al. that are cumbersome and slow because they require multiple rotations of a handle for linearly reducing a spinal rod. The '995 patent requires the surgeon to manipulate two separate handles in order to linearly advance a drive rod and also rotate the drive rod to lock a cap in a coupling member. The use of two handles complicates the tool and the girth of the instrument typically requires the surgeon to occupy both hands in use. The advantage of the improved drive tool apparatus is actuation through a pawl on a unitary drive rod by a mechanical linkage allowing for rapid reduction. The reduction of the drive rod is further expedited in that it can be manually advanced distally through the drive tool while being mechanically restrained from moving in the proximal direction. Manual advancement is undertaken until it is determined that the mechanical advantage of the actuating mechanism is required.

Unlike the threaded drive and rongeur style persuaders, the improved drive tool apparatus uses a single unitary drive rod or shaft made from a single piece of metal that both drives the spinal rod linearly down and rotates the cap or locking device in place. The simplified unitary drive rod approach eliminates multiple parts, improves reliability, and simplifies operation of the tool. In addition, once the locking device is finally locked in place, the drive rod quickly and easily mechanically disengages from the drive tool due to the orientation of the drive surface relative to both the drive and stop pawls.

The improved drive tool apparatus has a unique actuating mechanism that utilizes an engagement of a pawl on a rack or drive portion of a drive rod. The drive pawl is freely rotatable allowing the pawl to engage the drive portion when necessary while allowing disengagement when the actuation lever is released. The lock or stop device prevents displacement of the drive rod in the proximal direction during the return stroke of the pawl on the rack of the unitary drive rod. The actuating mechanism is a hybrid mechanism utilizing both a mechanical leverage and a rotatable pawl linkage that provides dynamic rotary and linear mechanical engagement simultaneously during linear displacement in the distal direction. Finally, the improved drive tool apparatus features an attachment mechanism for quick connection and disconnection to screw extenders and spinal screw assemblies which is desirable in MISS surgeries. The attachment mechanism allows the drive tool to rapidly attach and detach from screw extenders or yoke manipulators by depression of a simple trigger. The quick connection feature allows one drive tool to easily be transferred to multiple different screw assemblies, present in most spinal rod stabilization procedures. The quick connect feature eliminates complicated attachment to greatly reduce time and simplify the surgery.

The following location and direction convention will be used through out the drawings and their descriptions. In describing the surgical instrument of the present invention, the term "proximal" P refers to a direction of the tool or instrument away from the patient and towards the user while the term "distal" D refers to a direction of the tool or instrument towards the patient and away from the user.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

Figure 2:
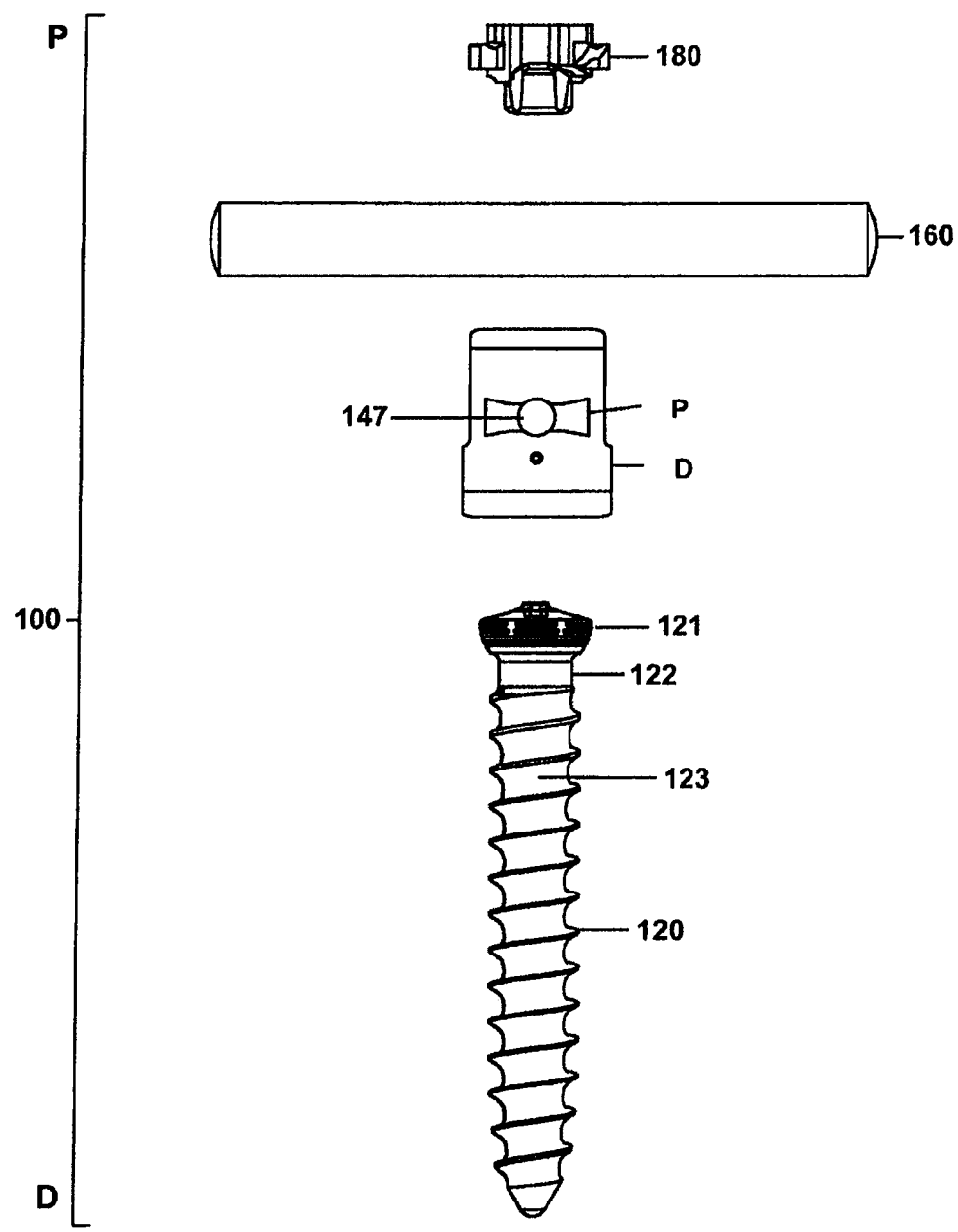
FIG. 2 illustrates an exploded side view of the pedicle screw assembly.

FIGS. 1 and 2 provide exploded views of a pedicle screw assembly 100. The pedicle screw assembly is fully described in U.S. patent application Ser. No. 10/358,530 which is incorporated by reference as if reproduced in its entirety herein.

Figure 3A:
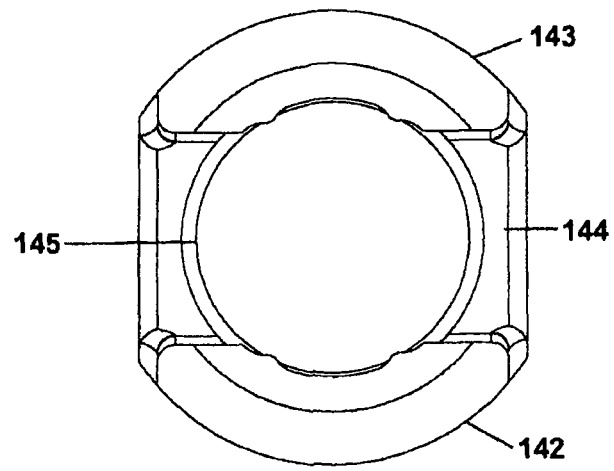
FIG. 3a is a top view of a coupling member of the pedicle screw assembly.
Figure 3B:
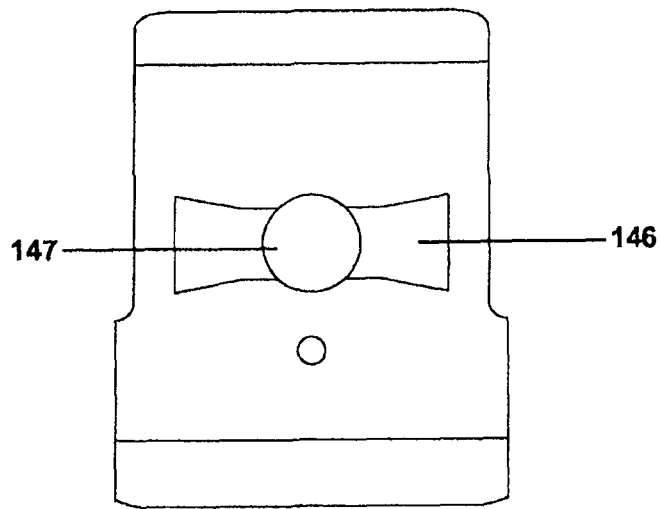
FIG. 3b is a front view of the coupling member.
Figure 5:
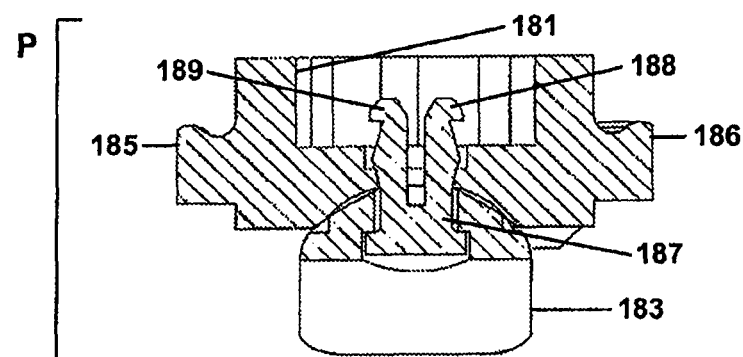
FIG. 5 is a front sectional view of the locking device or cap.
Figure 4:
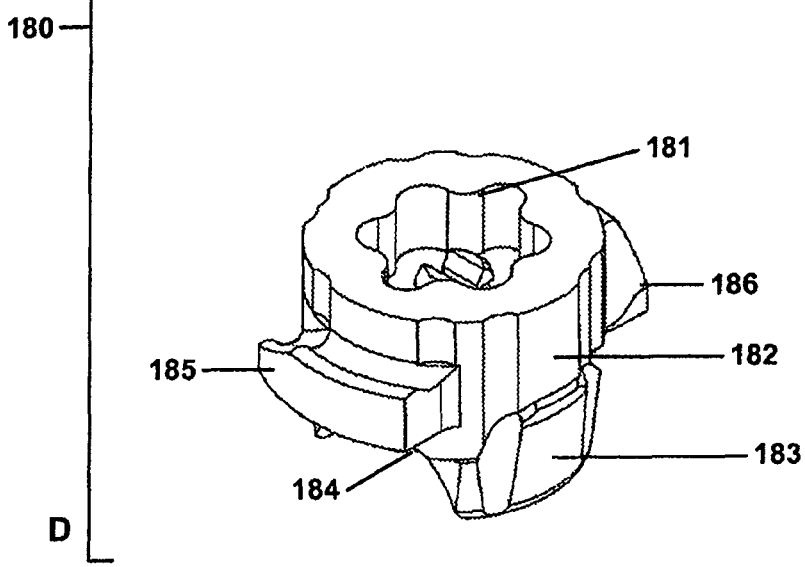
FIG. 4 is a perspective view of a locking device or cap of the pedicle screw assembly.

The pedicle screw assembly 100 includes a bone anchor 120, a coupling member or yoke 140, a connecting member or rod 160 and a locking device or cap 180. Bone anchor 120 includes a head portion 121, a shank portion 122 depending from the head portion, and a threaded portion 123 depending from the shank. Coupling member or yoke 140 includes a body portion 141, two arms 142 and 143 connected to body 141 adjacent distal end D forming a u-shaped channel 144 for receiving rod 160. The coupling member 140 of FIG. 3 includes an anchor bore 145 for receiving bone anchor 120. The coupling member 140 includes an instrument engagement portion in the form of slot 146 and a bore 147. Connecting member or rod 160 is circular in cross section with a smooth exterior surface and may come in any number of lengths to satisfy surgeon requirements. In FIGS. 4, 5 and 7a the locking device or cap 180 includes inner wall surface 181 for engaging a drive apparatus and an outer wall surface 182. The cap has a saddle portion 183 with a rod engagement surface 184. Adjacent the proximal end of the locking device are flanges 185,186 which engage interior grooves 148 in coupling member 140 and when rotated serve to lock the rod 160 between the rod engaging surface 184 and the u-shaped channel 144. The proximal portion of the cap and the saddle portion are attached by a pin 187 with splaying arms 188 and 189.

In addition it is contemplated that the bone anchor 120 may be cannulated 126 thus providing a pathway through the entire anchor member 120 should a guidewire attached to a specifically targeted surgical site wish to be employed.

Figure 6:
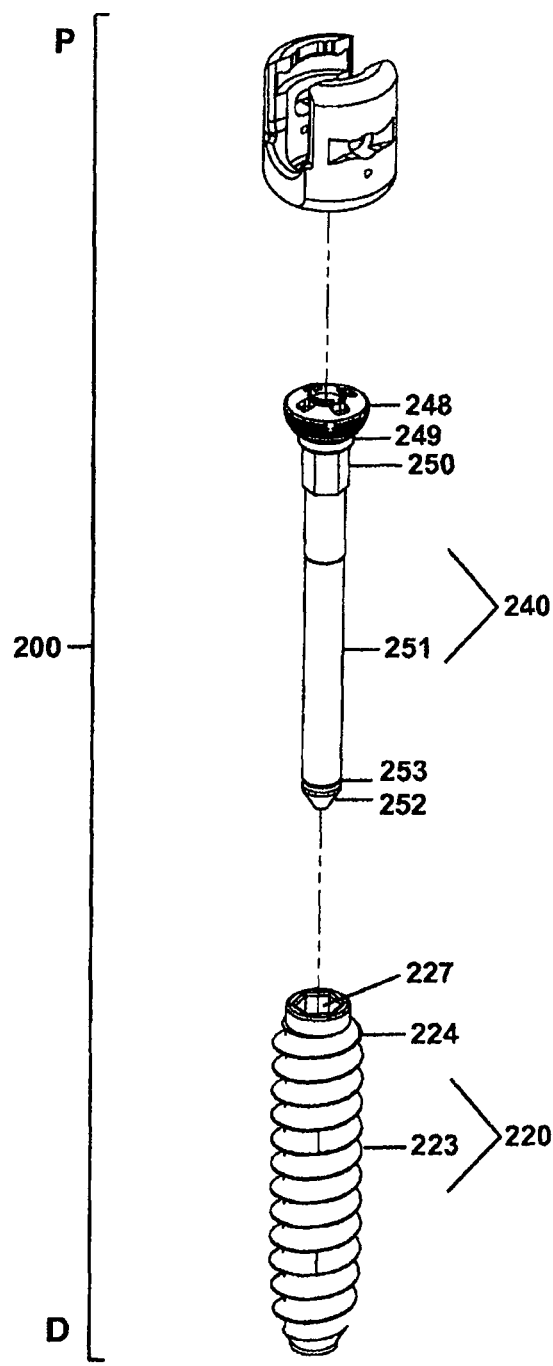
FIG. 6 is an exploded view of an alternative pedicle assembly (swage embodiment)
Figure 7:
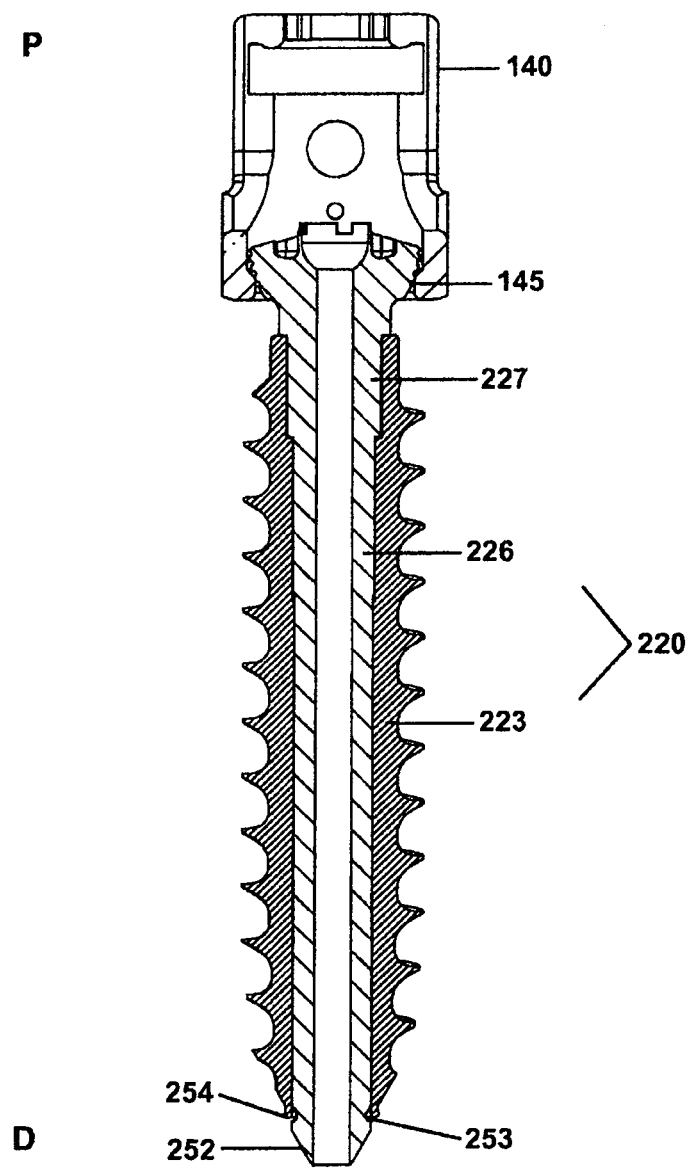
FIG. 7 is a front sectional view of the assembly of FIG. 6.
Figure 7A:
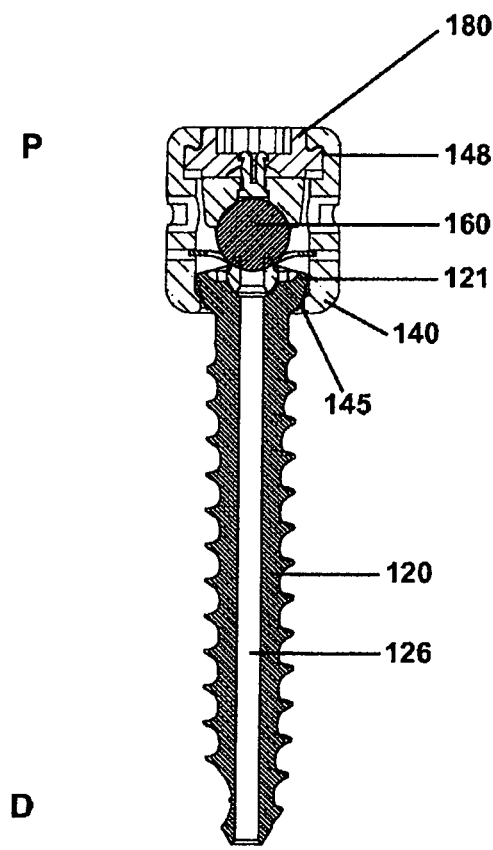
FIG. 7a is a side sectional view of the assembly of FIG. 6.

FIGS. 6 and 7 provide another embodiment of a pedicle screw assembly 200. The assembly 200 contains the exact same components of assembly 100 (coupling member 140, rod 160, and locking device 180) with the exception of the bone anchor. The bone anchor 220 of assembly 200 includes a threaded portion 223, and a shaft portion 240. Threaded portion includes external threads 224 for anchoring into bone, and a crimping or swaging lip 254 for attaching the threaded portion 223 to the shaft portion 240. The interior of the threaded portion is cannulated 226 having an inside diameter that is constant from the distal end of threaded portion 223 to adjacent the proximal end. At the proximal end there is a hexagonal opening 227 to mate with the hexagonal section 250 of shaft portion 240. The shaft portion 240 is monolithic but has several sections including head section 248, neck section 249 depending from head section, hexagonal section 250 depending from neck section, and shaft 251 depending from hexagonal section 250. The shaft has a taper 252 at distal end D with a swaging or crimping groove 253 proximal and adjacent the taper 252.

After shaft portion 240 and threaded portion 220 are manufactured they are assembled and placed in sets of various external thread (224) diameters. The shaft portion 240 is fed through anchor bore 145 of coupling member 140, the head section 248 of shaft portion 240 is larger than that of distal end D of anchor bore 145 of coupling member 140 and will come to rest in distal end of coupling member 140. The shaft portion 240 is then fed through cannulated section 226 of bone anchor 220 until proximal end of threaded portion 220 abuts distal end of neck section 249 of shaft portion 240. A common method of swaging or crimping is performed on the swaging or crimping lip 254 until all of the lip material fills the swaging or crimping groove 253 of shaft portion 240. Shaft portion 240 can no longer advance proximally or distally due to the relationship of the neck section 249 and the proximal end of bone anchor 220 and the swaging or crimping of lip 254 into groove 253. The ability to rotate both the shaft portion 240 and the threaded portion 220 simultaneously is possible due to the mating surfaces of the hexagonal section 250 of shaft portion 240 and hexagonal opening 227 of bone anchor 220.

The advantage of pedicle screw assembly 200 lies in that virtually any diameter external thread 224 of threaded section 223 can be employed. Since the threaded section 223 of bone anchor assembly 200 is not initially integral with shaft section 240 it need not be passed through anchor bore 145 of coupling member or yoke 140. The ability select from screws with larger diameters, makes the screw ideal for patients with large anatomies, revision surgeries requiring rescue screws of large diameter and anchoring of screws in the ilium of the patient. Screw assemblies 200 would be provided fully assembled to surgeons in sets with varying diameter external threads 224 thus allowing the surgeon to select the desired diameter best suited for the given operation. Screw assembly 200 after assembled is thereafter employed in the exact same manner as screw assembly 100. The method of employing the drive tool apparatus 1200 and other instruments of the present invention will be hereafter described using the numeration of pedicle screw assembly 100, but is not to be considered limiting.

Referring now to FIG. 7a, in use, bone anchor 120 is inserted through anchor bore 145 of coupling member 140. The larger diameter of head portion 121 of bone anchor 120 is larger than bone anchor bore 145 of coupling member 140 and thus bone anchor 120 is unable pass through. Two or more bone anchors 120 are driven into the adjacent bones to be stabilized. A connecting member or rod 160 is then placed in the u-shaped channels 144 of respective coupling members 140, a locking device or cap 180 is then inserted into one of the coupling members 140 and rotated clockwise 10-45 degrees to temporarily capture connecting member 160 in coupling member 140. After manipulating the spinal rod 160 for the desired results, the temporary locking step is repeated with the second pedicle screw assembly 100.

The difficulties that arise during these types of surgeries often occur during the stage of inserting and reducing the rod 160 into the connecting members 140. This step is often complicated by the fact that the pedicle screw assembly is almost certain to be surrounded by the patient's tissues, making a path to the coupling member difficult to navigate. It is at this stage that surgeons often look for instruments to assist in efficiently urging or persuading the rod 160 into the yokes 140.

The improved drive tool apparatus 1200 is provided for the purpose of directly addressing the surgical need for an efficient instrument to persuade a connecting element 160 in a minimally invasive spinal surgery (MISS). Drive tool apparatus 1200 includes yoke manipulator 1100 and drive rod 1300, which are shown in FIG. 8 & FIG. 29-33. The improved drive tool apparatus 1200 allows rigid attachment to a screw extender 1100 and screw assembly 100 during rotation, distraction, contraction and reduction of a connecting element 160 common in MISS. Drive tool 1200 may also be employed in rotating the spine as is common practice when treating severe trauma or disease such as scoliosis. The improved drive tool apparatus 1200 is able to resist detachment from the screw assembly in a manner superior to other devices enabling the surgeon to both reduce and rotate the spinal connecting element 160.

In minimally invasive spine surgery a guide wire often is inserted into a patient and maneuvered toward the vertebra while fluoroscopy is employed to pinpoint and verify an accurate surgical location. Surrounding tissue is then sequentially dilated. Once the tissue is dilated, cannulated tools may be utilized to prepare the pedicle for a screw assembly 100 (e.g. pedicle probes, awls, taps, etc.) A cannulated bone anchor 120, moveably attached to coupling member 140 through anchor bore 145 is slid over the guide wire distally until it reaches the surgical site. The use of a guide wire ultimately reduces the amount of tissue affected thus reducing recovery time. Minimally Invasive Spine Surgery may also be conducted without a guidewire relying on just the use of fluoroscopy. In either case, coupling member or yoke 140 needs to be attached to a tool such that the coupling member or yoke 140 may be manipulated by the operator deep within the patient.

Figure 8:
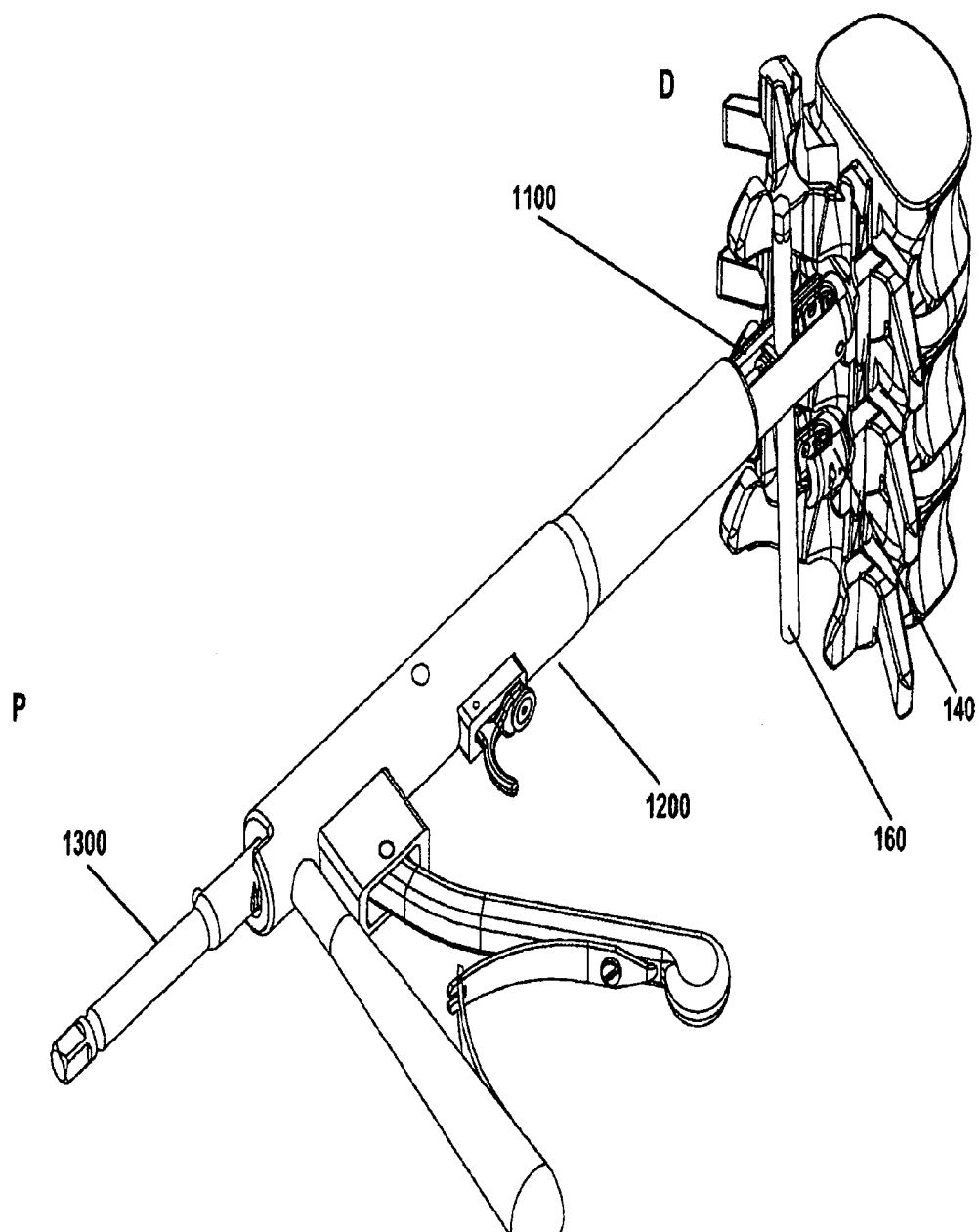
FIG. 8 is a perspective view of a drive tool with a drive rod, anchor extension and the pedicle screw assembly.
Figure 9:
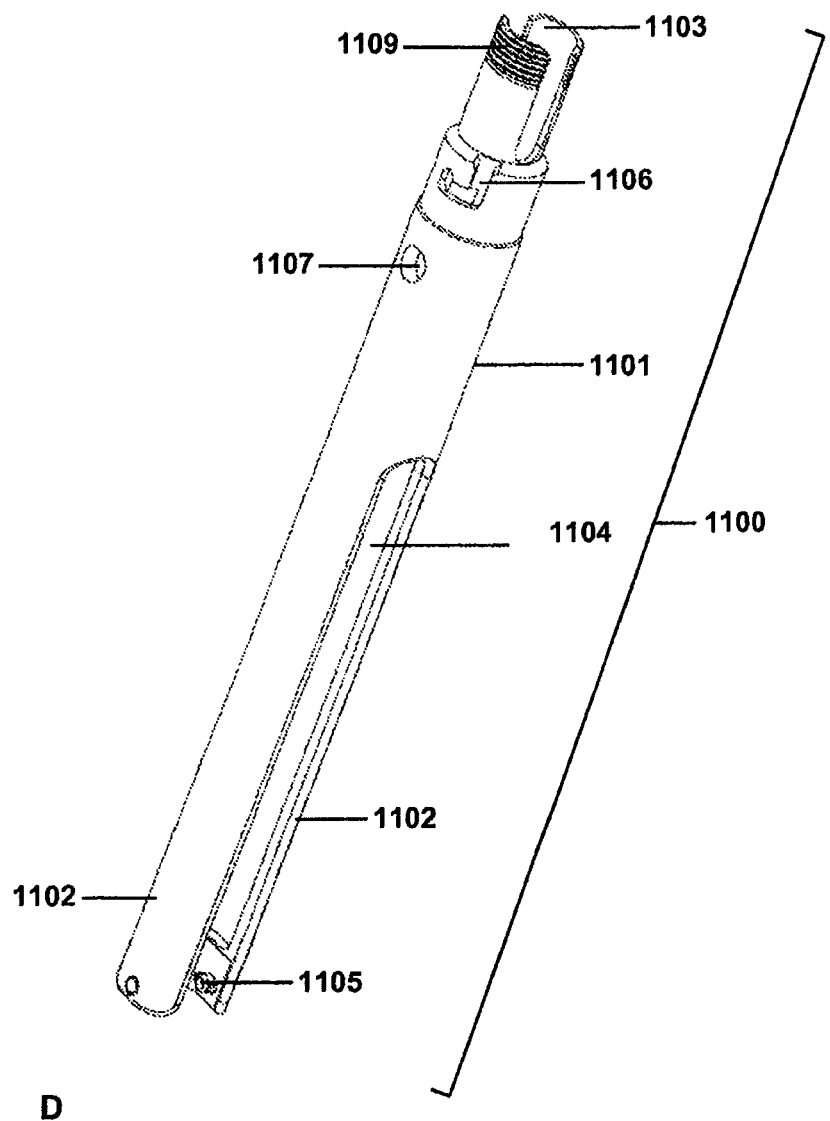
FIG. 9 is a perspective view of the anchor extension or yoke manipulator.

Screw extender or yoke manipulator 1100 shown in FIG. 8 and FIG. 9 has a proximal end P and a distal end D. Screw or shaft extender 1100 includes body portion 1101, arms 1102 depending distally from body 1101 defining opposing u-shaped slots 1104, and a shaft or bore 1103 extending from the proximal end to the distal end creating a cannula or working corridor. In addition, screw extender 1100 accommodates attachment to a wide variety instruments with three different instrument attachment structures; bayonet connection slot 1106, threaded connection 1109 and drive tool connection hole 1107. For the purpose of the present invention particular attention may be paid to the drive tool connection hole 1107. The connection hole 1107 is a bore or hole through one side of the extender body 1101 of the screw extender 1100. Alternatively, the hole 1107 could be in the form of depressions or indentations in the manipulator shaft 1101 in a variety of other varying closed geometries such as, but not limited to, squares, hexagons, etc. The drive tool connection hole allows for rapid connect and disconnect to a variety of instruments and in particular the preferred drive tool apparatus 1200 via the screw extender attachment portion 1201 on drive tool apparatus 1200. The simple hole 1107 in connection with the attachment portion or releasable connector device 1201 performs the critical functions of simplifying and accelerating the pace of the surgery by allowing the operator to pull a trigger and immediately remove drive tool 1200 from extender 1100.

Screw extender 1100 is attached to coupling member 140 by a coupling member retaining structure 1105 on the inner surface of arms 1102 at distal end D that releasably mates in snap-fit connection with bore 147 of coupling member 140 of pedicle screw assembly 100. It is contemplated that coupling member retaining structure 1105 may include, but not limited to, a boss, recess, flange, or any other structure that is suitable to mate with a complimentary structure on coupling member 140.

The screw extenders arms 1102 are resiliently splayed away from one another with an extender arm spreader instrument (not shown). The extender 1100 is then placed over the coupling member 140 so that the slots 1104 in the screw extender 1100 are radially aligned with the u-shaped channel 144 of coupling member 140 and coupling member retaining structure 1105 is positioned in radial and longitudinal adjacency to bore 147. The arms 1102 of screw extender 1100 are then allowed to resiliently return to their original position by the removal of the spreader instrument leaving screw extender 1100 and coupling member 140 rigidly attached in snap-fit engagement.

The screw extender 1100 may be used to manipulate the coupling member 140, previously assembled to anchor member 120, during the insertion process. If cannulated, the anchor 120, coupling member 140, and extender 1100 are fed down the guide wire to the surgical site. An anchor insertion device may then be attached to the extender 1100 at any of the three instrument attachment structure locations 1106, 1107, or 1109. The engagement of the insertion device (not shown) to the anchor 120 and engagement of extender 1100 to coupling member 140 provides a rigid construct.

Referring to FIGS. 8, 10a, 11, and 12, the long slot 1104 of the manipulator 1100 provides the surgeon with ample clearance and visualization of the surgical site which are beneficial during insertion of connecting member 160. The insertion of the rod or connecting member 160 will be more fully described when describing the drive tool 1200 in more detail hereinafter. It is contemplated that the slots 1104 of the extenders 1100 may be of varying lengths. In fact, as long as one of the extenders 1100 provides enough clearance for the connecting member 160 to be initially inserted, the other extender(s) 1100 may be provided with shorter slots 1104 or perhaps may include a slot on only one side. In any event, whether the slots 1104 are short or long, they must allow for adequate access during the process of passing the connecting member 160 into the coupling members 140.

Figure 10A:
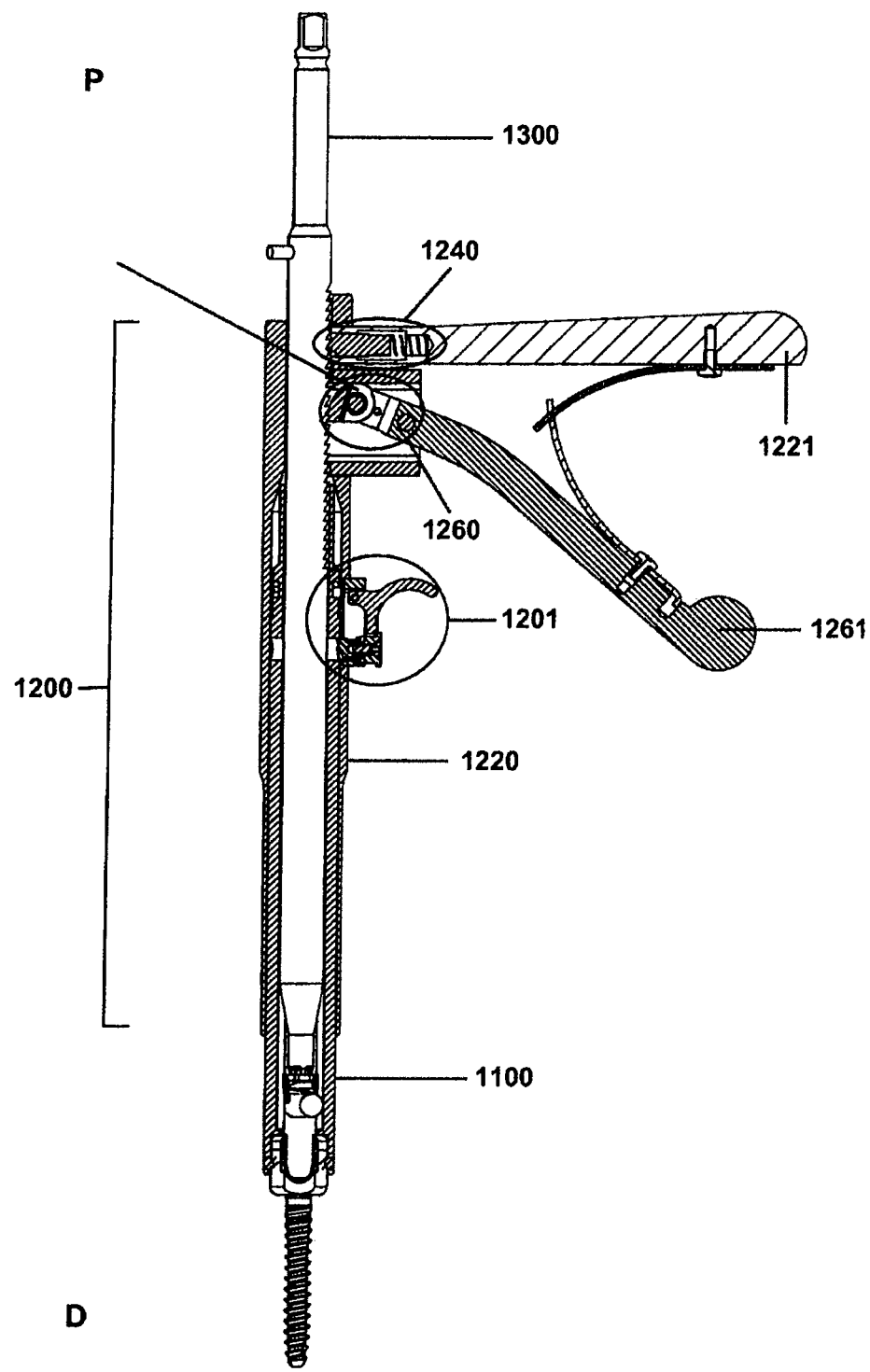
FIG. 10a is a front side sectional view of the drive tool, drive rod, anchor extension and pedicle screw assembly.
Figure 12:
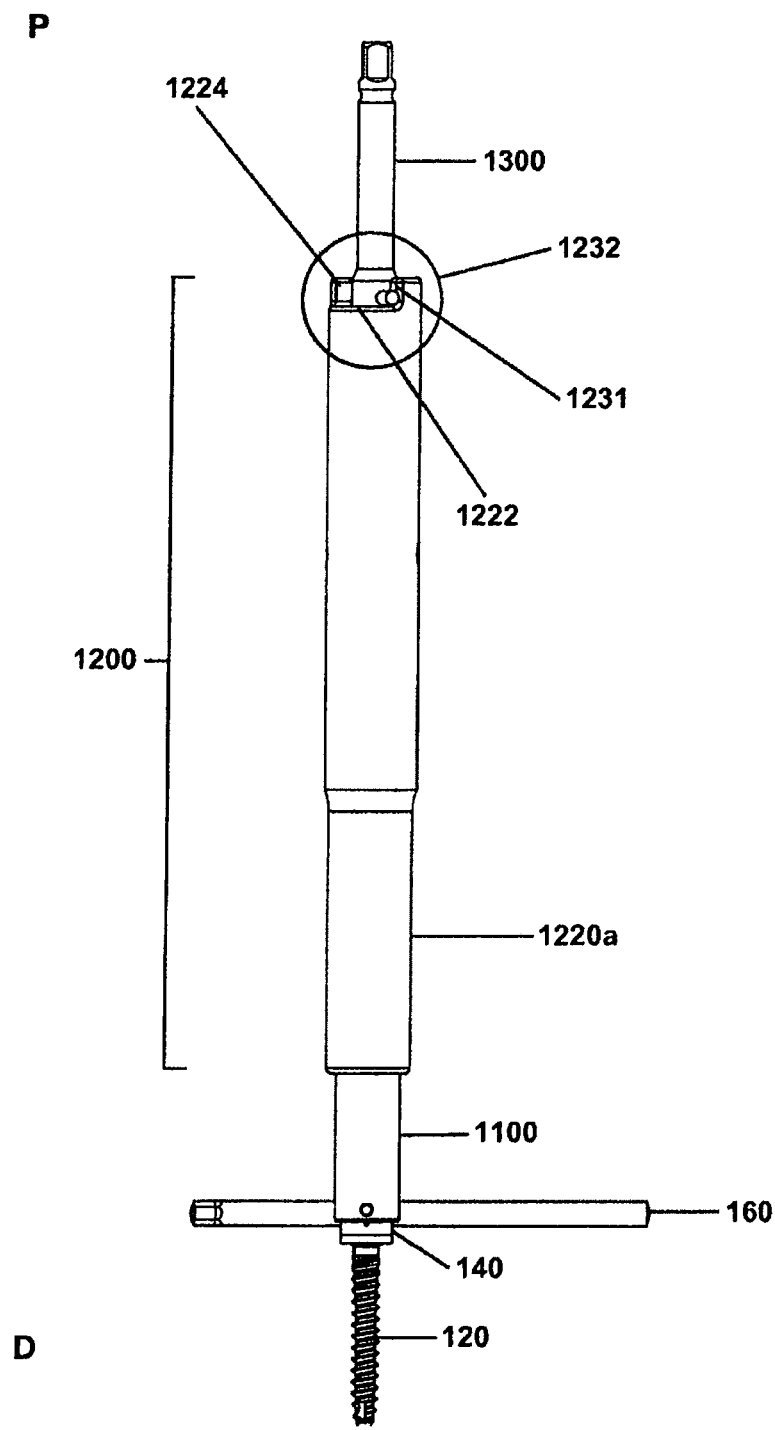
FIG. 12 is a left side view of the drive tool, drive rod, anchor extension and pedicle screw assembly.

The drive tool apparatus 1200 of the present invention has a distal direction D, proximal direction P, and consists principally of a screw extender attachment portion 1201, elongate shaft assembly or body 1220, the unitary drive rod 1300, mechanical linkage portion 1260, stationary grip 1221, drive actuator lever 1261 and mechanical guide portion 1232 as shown in FIGS. 10a and 12. The drive tool apparatus 1200 is used in concert with screw extender 1100. Screw extender 1100 is designed for minimally invasive spine surgery but may be utilized in open surgical situations which will be addressed later. Screw extender 1100 once rigidly attached to drive tool 1200 provide the operator a working corridor to the implantation site with the ability to manipulate the implant while allowing other instruments to be employed therethrough.

The elongate shaft assembly or body 1220 of the drive tool apparatus 1200 has distal end D and proximal end P and is provided for the purpose of providing a structural member intended to resist longitudinal compression forces created during the rod reduction process and to provide structure for accommodating components that can be attached to or rotated relative to body 1220. The body or shaft assembly 1220 is a substantially hollow tube with varying diameters and wall thicknesses. The elongate body 1220 or elongate shaft assembly also provides rectangular through hole 1271 to accommodate mechanical linkage portion support 1270, rectangular flat 1208 accommodating attachment portion structure 1225, and a partial bore 1272 with slot 127 to accommodate stop portion 1274 located inside stationary grip 1221 mounted to body 1220 adjacent the proximal end. Finally, the shaft assembly 1220 provides a mechanical guide flat 1222 for unitary drive rod 1300. Alternatively, the attachment support structure 1225 and mechanical linkage portion support 1270 could be machined as an integral part of elongate body 1220.

Figure 26:
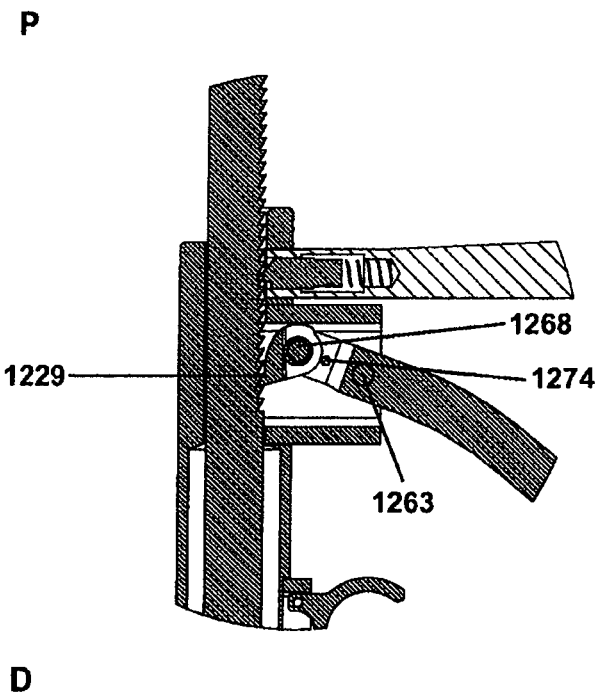
FIG. 26 is a front side sectional view of drive pawl engaging the drive portion of the drive rod.
Figures 27A, 27B:
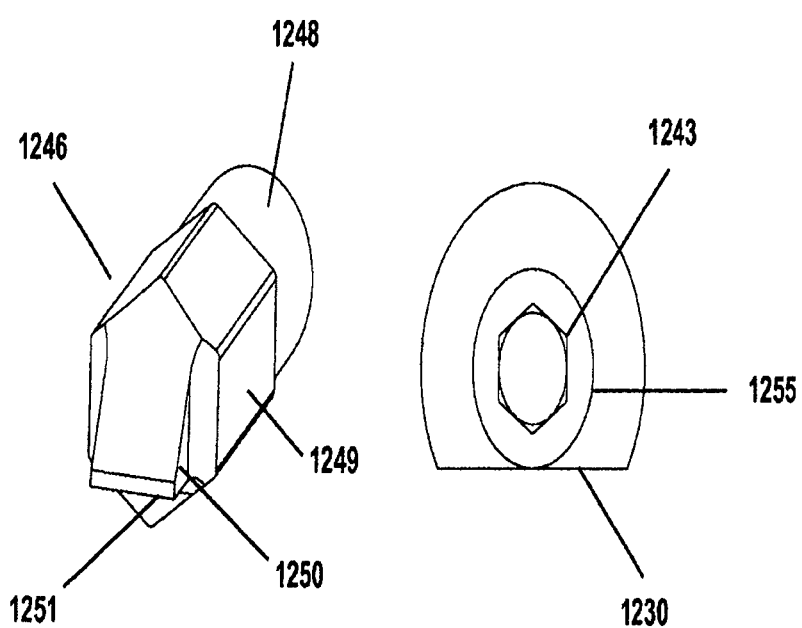
FIG. 27a is a perspective view of the stop pawl of the drive tool.
FIG. 27b is a left side view of the stationary grip of the drive tool.

The main tube body 1307 has significant wall thicknesses to support the high compressive loads created by drive actuator pawl 1229 on the unitary drive rod member 1300, as shown in FIG. 26. High compressive loads are created because the main tube body 1220 provides a force to counter and balance the force exerted by the drive actuator pawl 1229 on the unitary drive rod member 1300 on the spinal rod 160.

Figure 13:
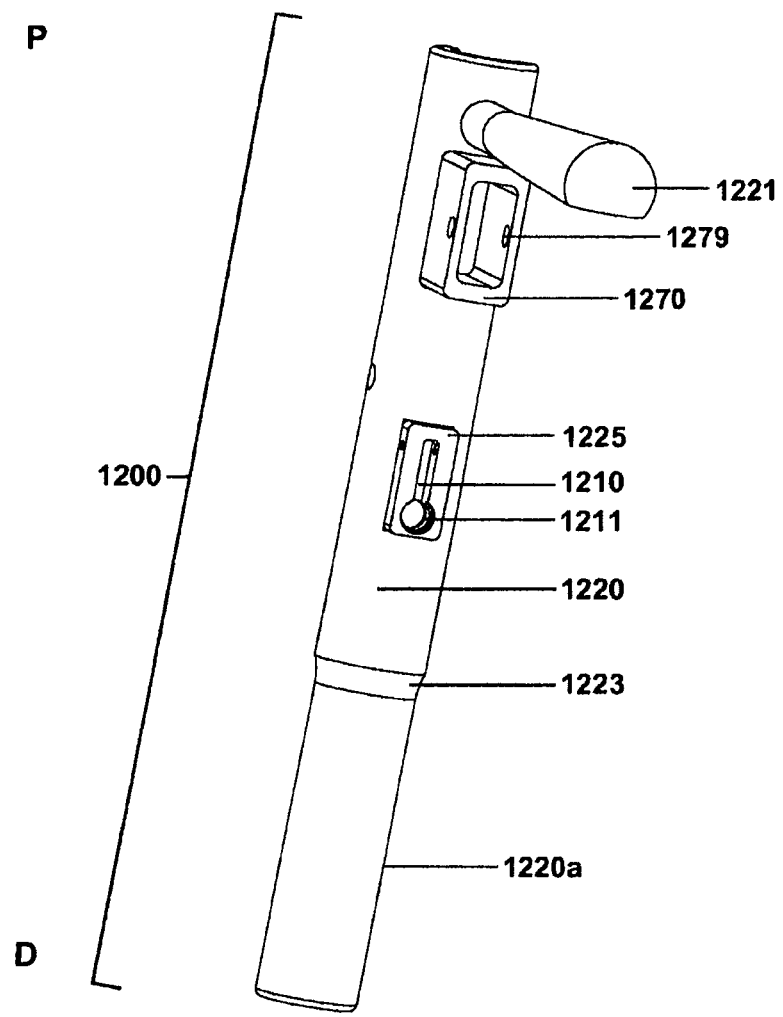
FIG. 13 is a perspective view of the drive tool elongate body with attachment structures/portions and the stationary grip.

As shown in FIG. 13, elongate body 1220 has a tapered section 1223 which transitions to the distal tube body 1220a. Distal tube body 1220a has a reduced wall diameter because distal portion of distal tube body 1220a will enter the furthest depth in the body of the patient. The smaller diameter reduces the footprint of elongate shaft assembly 1220 thus disrupting less tissue upon insertion of drive tool 1200 into the patient. The distal tube body 1220a can have a reduced wall thickness and smaller diameter because the screw extender 1100 provides additional significant structural support against longitudinal compression.

Referring now to FIGS. 10a-13. Elongate shaft assembly or body 1220 also provides a mechanical guide portion 1232 for rotational engagement of the unitary drive rod member 1300 as shown in FIG. 12. Elongate shaft assembly or body's 1220 mechanical guide portion 1232 cooperates with an alignment pin 1304 of drive rod 1300 facilitating alignment and providing both a visual means for indicating mechanical engagement and disengagement of the unitary drive rod member 1300 drive portion 1302 with a drive actuator pawl 1229 of the mechanical linkage portion 1260 and lock, portion 1240, as well as the orientation of locking device 180 relative to coupling member 140. After the reduction of the rod 160 on to the coupling member 140 and during the locking of the locking device or cap 180, flat 1222 on body 1220 provides a zero degree wall 1231 that gives the operator a visual (and starting point) reference with respect to the position of cap 180. Mechanical guide portion 1232 has hard stop 1224 representing 100 degrees of revolution letting the operator know that cap 180 is fully locked in coupling member 140 and rod is captured when alignment pin 1304 abuts hard stop 1224. Accordingly, the wall 1231 and hard stop 1224 are preferably circumferentially spaced around the top of the elongate body 1220, as seen best in FIGS. 12 and 28a-28c.

Figure 14:
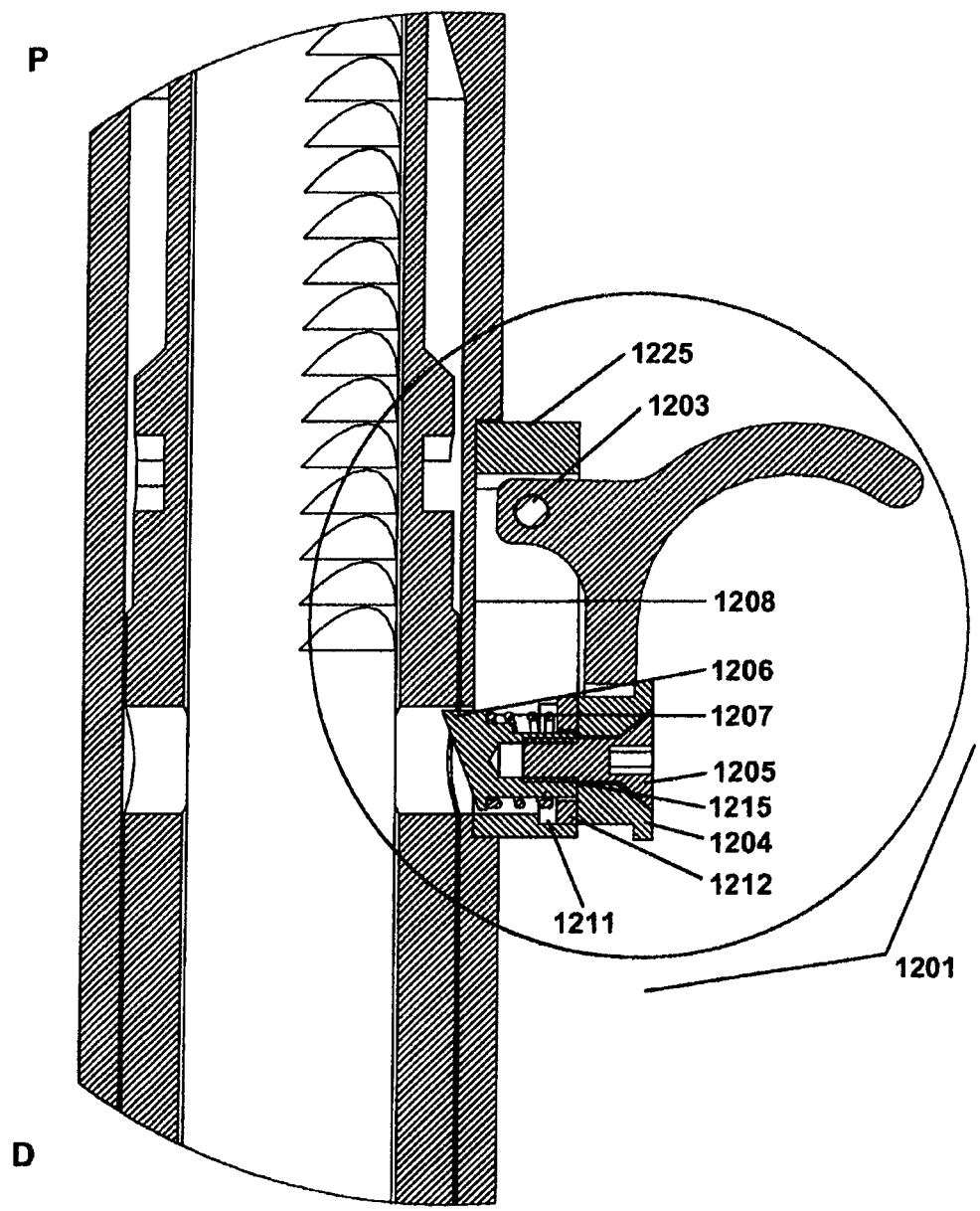
FIG. 14 is a front side sectional view of the drive tool attachment portion.
Figure 15:
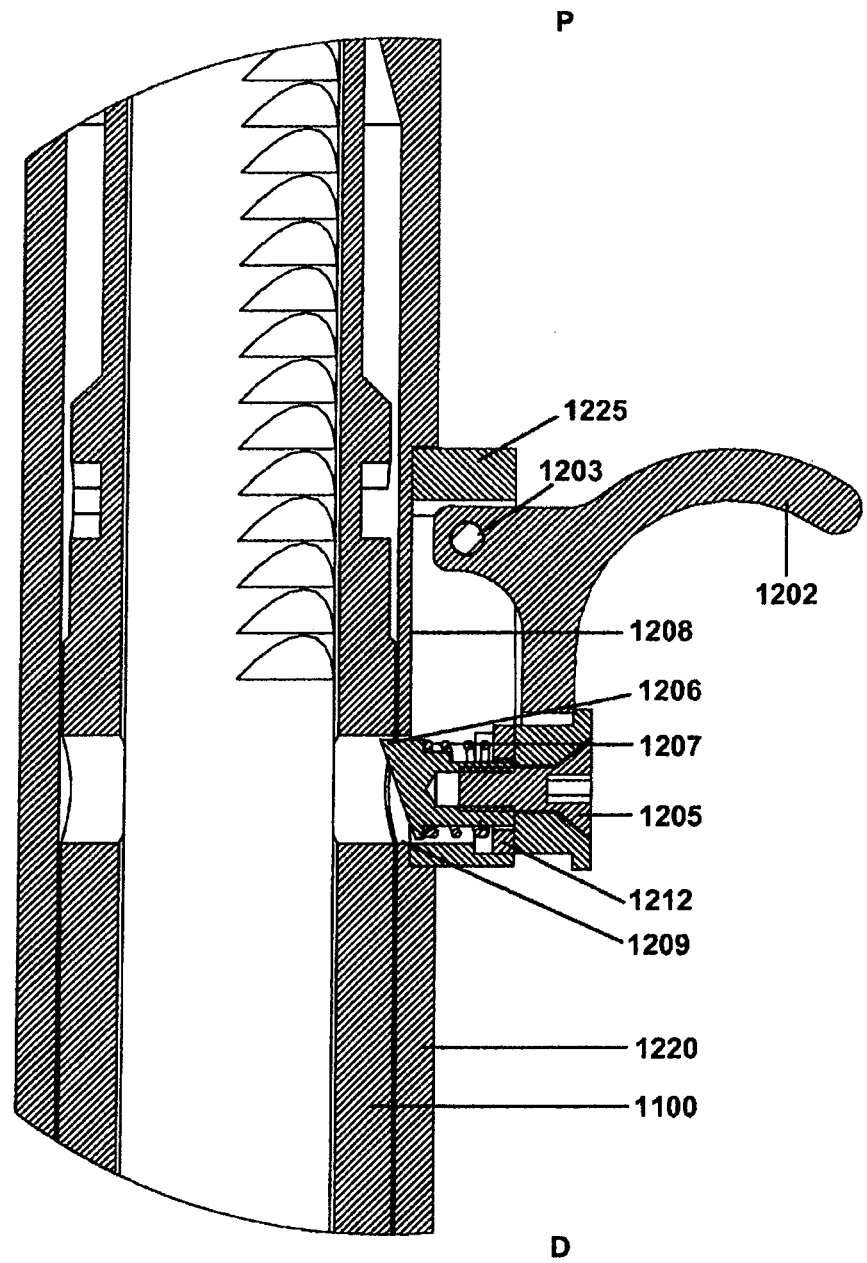
FIG. 15 is a front side sectional view of the drive tool attachment portion.

The screw extender attachment portion 1201 as shown in FIGS. 14 and 15, and discussed in detail below, provides for the quick capture and release of the pedicle screw extender 1100 to the drive tool 1200. The attachment portion 1201, externally visible as a trigger, is attached to the elongate shaft assembly or body 1220 at attachment support structure 1225 as seen in FIG. 15.

Referring now to FIGS. 10b-13, attachment support structure 1225 is rectangular in shape and is welded onto assembly body 1220 in rectangular flat 1208. Rectangular flat 1208 has a throughbore 1209 to receive the catch 1206 of attachment portion 1201. Attachment support structure 1225 has a keyhole shaped opening 1210 therethrough that houses the screw extender attachment portion 1201. Distal end of keyhole shaped opening 1210 includes a threaded bore 1211 which receives threaded sleeve 1212.

Referring now to FIGS. 14 and 15, the attachment portion 1201 includes trigger 1202, attachment pin 1203, attachment collar 1204, threaded sleeve 1212, adjustment screw 1205, catch 1206, and spring 1207. The movement of catch 1206 in and out of drive tool connection hole 1107 of screw extender 1100, when positioned adjacent to the through bore 1209, allows the drive tool 1200 to be easily attached and detached to screw extender 1100. The spring 1207 urges the catch 1206 into the drive tool connection hole when the trigger 1202 is released.

The surgeon operates attachment mechanism portion 1201 by applying a force in proximal direction to trigger 1202. Trigger 1202 pivots about attachment pin 1203 moving the distal end of trigger 1202 away from the body 1220 of drive tool 1200 which in turn engages attachment collar 1204, as illustrated in FIG. 8, urging the attachment collar 1204 away from drive tool 1200. The threaded engagement 1215 of attachment collar 1204 and catch 1206 forces the entire sub assembly to move in the direction away from the screw extender thus catch 1206 mechanically disengages from drive tool connection hole 1107 in screw extender 1100. The drive tool apparatus 1200 can then be pulled in a proximal direction easily disengaging from screw extender 1100. Once the operator releases the trigger 1202, with the drive tool connection hole 1107 adjacent to the through bore 1209, the spring 1207 urges collar 1204, screw 1209 and catch 1206 back toward the inner shaft of drive tool 1200. The attachment mechanism 1201 can then mechanically reconnect the screw extender 1100 to drive tool 1200 once the screw extender 1100 is shifted into position.

As shown in FIG. 14 and FIG. 15, the threaded sleeve 1212 prevents the entire attachment mechanism 1201 from detaching from attachment support structure 1225. Threaded sleeve 1212 is fixed to the attachment support structure 1225 of elongate shaft assembly or body 1220 because threaded sleeve 1212 is threaded into the attachment support structure 1225 at threaded bore 1211. The sub-assembly cannot escape because inner diameter of the threaded sleeve 1212 is smaller than the outer diameter of spring 1207 and catch 1206.

The attachment collar 1204, adjustment screw 1205, and catch 1206 are preferably threadably connected together thus allowing the entire sub-assembly to move in a direction transverse to the longitudinal axis of drive tool 1200. Alternatively, the sub-assembly could be one single machined part or a combination thereof.

Figure 16:
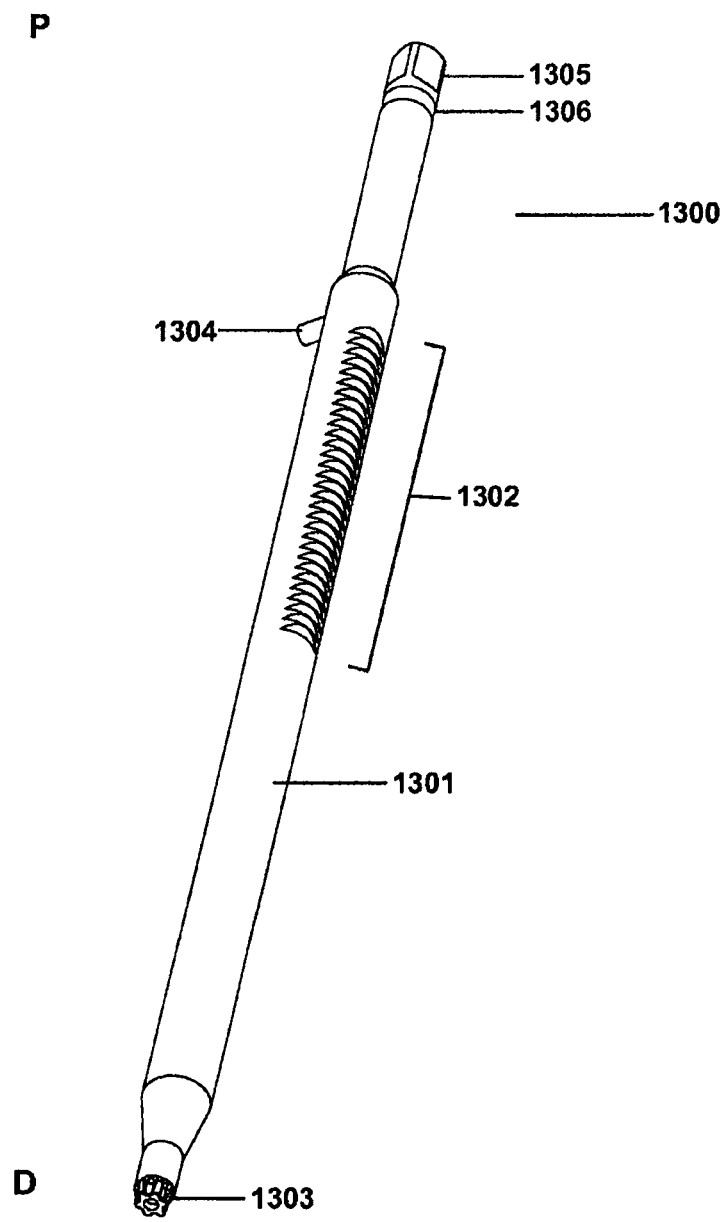
FIG. 16 is a perspective view of the drive rod.
Figure 17:
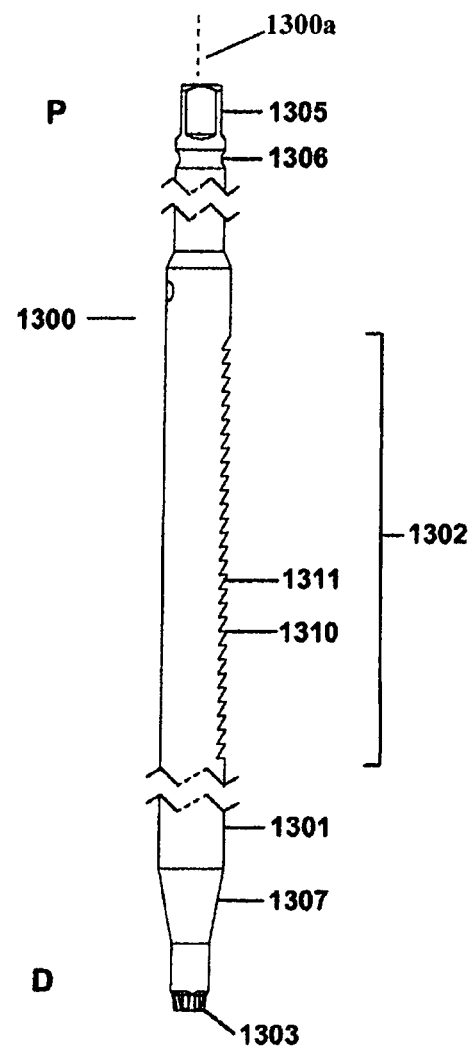
FIG. 17 is a front view of the drive rod.

Turning now to the unitary drive rod of FIGS. 16 and 17, unitary drive rod 1300 has a distal end D and proximal end P and is provided for the purpose of creating a compressive force used to drive locking device 180 on spinal rod 160 within coupling member or yoke 140 while in concert with drive tool 1200 and anchor extension 1100. The drive rod 1300 in its preferred embodiment is a single solid shaft 1301 with portions that do not move relative to one another including a drive portion 1302 mounted along a length of unitary drive rod, drive surface 1303 for engaging the cap or locking device 180, tool engagement end 1305 with groove 1306 for mating with an instrument, and alignment structure 1304 for engaging mechanical guide flat 1222 of drive tool 1200. The unitary drive rod 1300 is preferably formed from a single piece of homogenous metal to improve strength. Because multiple structural elements and linkages tend to increase the diameter of instruments used to apply force, the unitary drive rod 1300 requires minimal material while still providing the structural strength to resist torsion experienced during locking of cap 180.

In use unitary drive rod 1300 applies a compressive force through a locking device or cap 180 that mechanically engages the spinal rod 160. The application of compressive force through the locking device 180 or cap drives or persuades the rod 160 into yoke or coupling member 140. Once the rod 160 rests on bottom of u-shaped channel 144 of coupling member 140, drive rod 1300 is turned forcing the locking device 180 to turn simultaneously, with minimal relative motion between the drive rod 1300 and locking device 180, to either temporarily or permanently lock the locking device 180 or cap into the yoke or coupling member 140. The application of linear and rotary force by unitary drive rod 1300 through locking device or cap 180 to the spinal rod 160 provides several beneficial results. Not applying force directly to the spinal rod 160 but though the locking device or cap 180 more evenly distributes the compressive force or pressure over a larger area of rod 160. The compressive force required to drive the spinal rod 160 typically requires approximately a hundred pounds of force but in the sacral region may require hundreds of pounds of force. The distribution of pressure over rod 160 by cap or locking device 180 avoids large localized pressures being applied to rod 160 during the locking of rod 160 into coupling member or yoke 140.

The drive rod 1300 is sized to fit within screw extender 1100 and drive tool 1200. As shown in FIG. 16, drive rod 1300 includes a shaft 1301 and an alignment pin 1304. Alignment pin extends from drive rod 1300 transverse and preferably substantially orthogonal to the longitudinal axis 1300a of drive rod 1300. Alignment pin 1304 preferably takes the form of a pin, but other structures are contemplated such as a boss, flange, or any other structure complementary to the mechanical guide flat 1222 of drive rod tool 1200 for orienting the drive rod 1300.

Drive rod 1300 has drive portion 1302 which engages drive actuator pawl 1229 and stop pawl 1246. Drive portion 1302 has teeth with flat portion 1310 extending orthogonal to the drive rod axis 1300a and angled portion 1311 extending at an incline to the axis 1300a for forming a triangle in profile that mates with triangular portion 1284 of drive pawl 1229 and surface engagement end 1250 of stop pawl 1246. Drive rod 1300 may include a proximal engagement end 1305 for non-rotatable engagement with a removable grip, ratchet, or fixed grip instrument (not shown). The rectangular engagement end 1305 allows for the attachment of an "off-the-shelf" T-handle (not shown). Engagement end 1305 preferably allows for the attachment of a quarter inch drive T-handle with a quick disconnect. The quick disconnect utilizes groove 1306 distal and adjacent to engagement end 1305 to quickly connect and disconnect from a handle. The T-handle, once releasably attached to drive rod 1300, is used to apply torque to unitary drive rod 1300 for rotating locking devices such as cap 180. In alternate embodiments, the engagement end 1305 could take on numerous other geometric shapes, so long as it mates with an equivalent engagement surface of a handle, such as a hexagonal prism, or a triangular prism.

Figure 18:
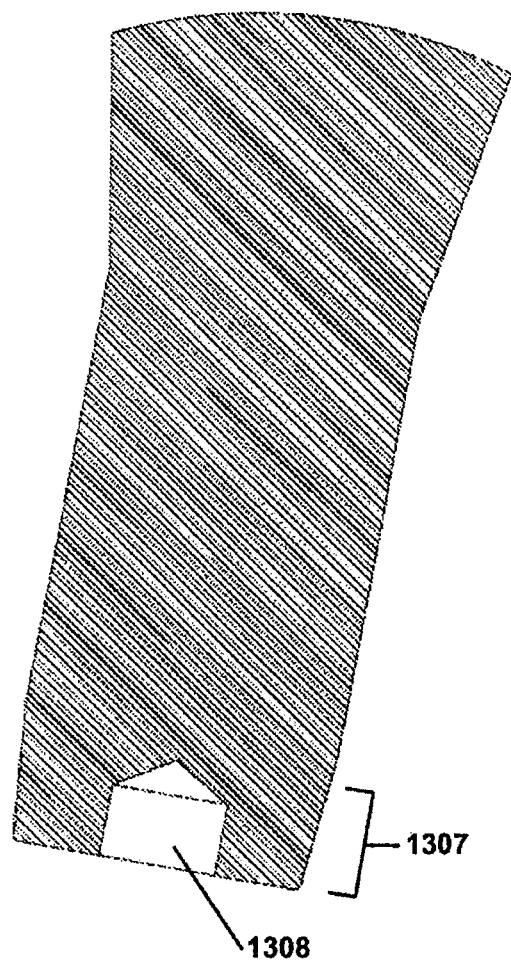
FIG. 18 is a perspective sectional view of the drive surface tip of the drive rod.

The drive rod 1300 is employed after being mated to the cap or locking device 180 at drive surface 1303. In the preferred embodiment a "stab and grab" technique or method is used to secure the locking device 180 to drive surface 1303. The preferred embodiment of drive surface 1303 located at distal end of drive rod 1300 is shown in FIGS. 17 & 18. The drive surface 1303 is tapered 1307 in profile and contains a bore 1308 providing clearance for pin 187 in coupling member 140. The drive rod 1300 is literally stabbed or forcefully friction fit within locking device 180 so that a line contact is formed between the drive surface 1303 and the inner wall 181 of locking device 180. The locking device 180 is temporarily fastened to the drive surface 1303 by slight deformation of the softer material (preferably titanium alloy) of the inner wall 181 of locking device 180 by the harder material (preferably stainless steel) of drive surface 1303 of unitary drive rod 1300.

Figure 19:
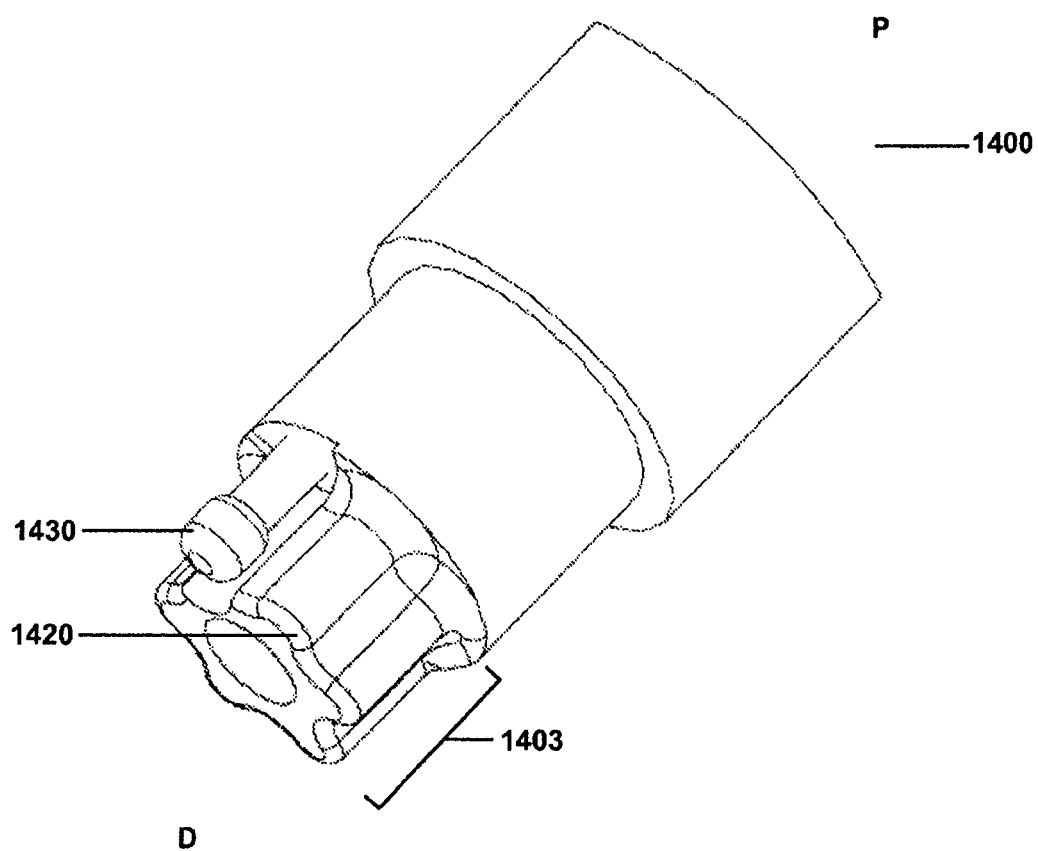
FIG. 19 is a perspective view of the nitinol pin embodiment of a drive rod.
Figure 20:
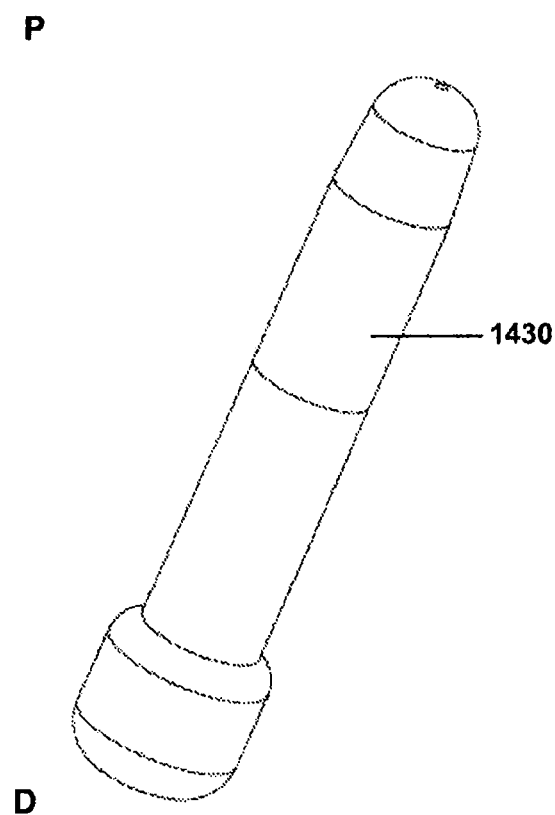
FIG. 20 is a perspective view of the nitinol pin of the drive rod of FIG. 19.

An alternative "stab and grab" method is used for the pin cap capture drive rod retention embodiment 1400 shown in FIGS. 19 and 20. The pin capture unitary drive rod 1400 has all the same elements of drive rod 1200 except with a differing drive surface and the manner in which pin capture drive rod 1400 mates with locking device 180. In this alternative embodiment the retention mechanism consists of the drive surface 1403 and a Nitinol pin 1430. Unlike drive rod 1200 the drive surface 1403 of pin capture drive 1400 is not tapered. In use, distal end D of pin cap capture drive rod 1400, is stabbed or moved in the distal direction toward the inner wall 181 of locking device 180. As the pin capture rod 1400 is advanced, the Nitinol pin 1430 resiliently deflects inward. This inward deflection creates a cantilever spring. The Nitinol pin 1430 resists inward deflection and thus makes a press fit on inner wall 181 of locking device 180 as the pin 1430 seeks its original position. The force of the Nitinol pin 1430 against inner wall 181 creates sufficient friction to hold the locking device 180 temporarily in place.

In the manufacture of pin capture drive rod 1400 one of the lobes 1420 of drive surface 1403 is omitted and a hole (not shown), slightly smaller than the outside diameter of pin 1430, is drilled in the open space where missing lobe 1420 would have been. The hole is drilled in the distal to proximal direction to equal length B of pin 1430. The pin 1430 is then press fit into the hole. The location of the pin 1430 in relationship to the adjacent lobes 1420 is critical in that should the drive rod 1400 be dropped or banged into something, pin 1430 will not be able to bend enough to plastically deform.

Materials other than Nitinol may be considered to make pin 1430 so long as those materials are bio-compatible, remain elastically deformable and do not yield under a radial bending force.

Figure 21:
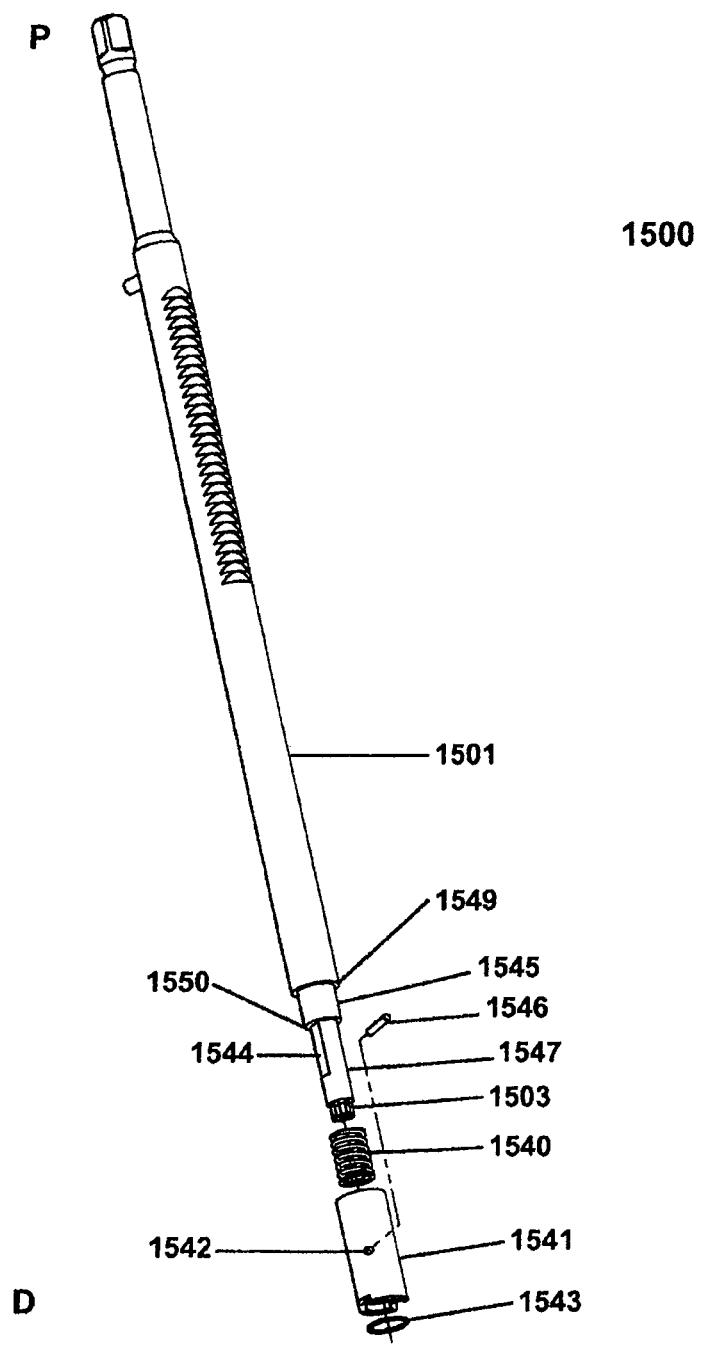
FIG. 21 is an exploded view of the sleeve capture drive rod embodiment.
Figures 22A, 22B:
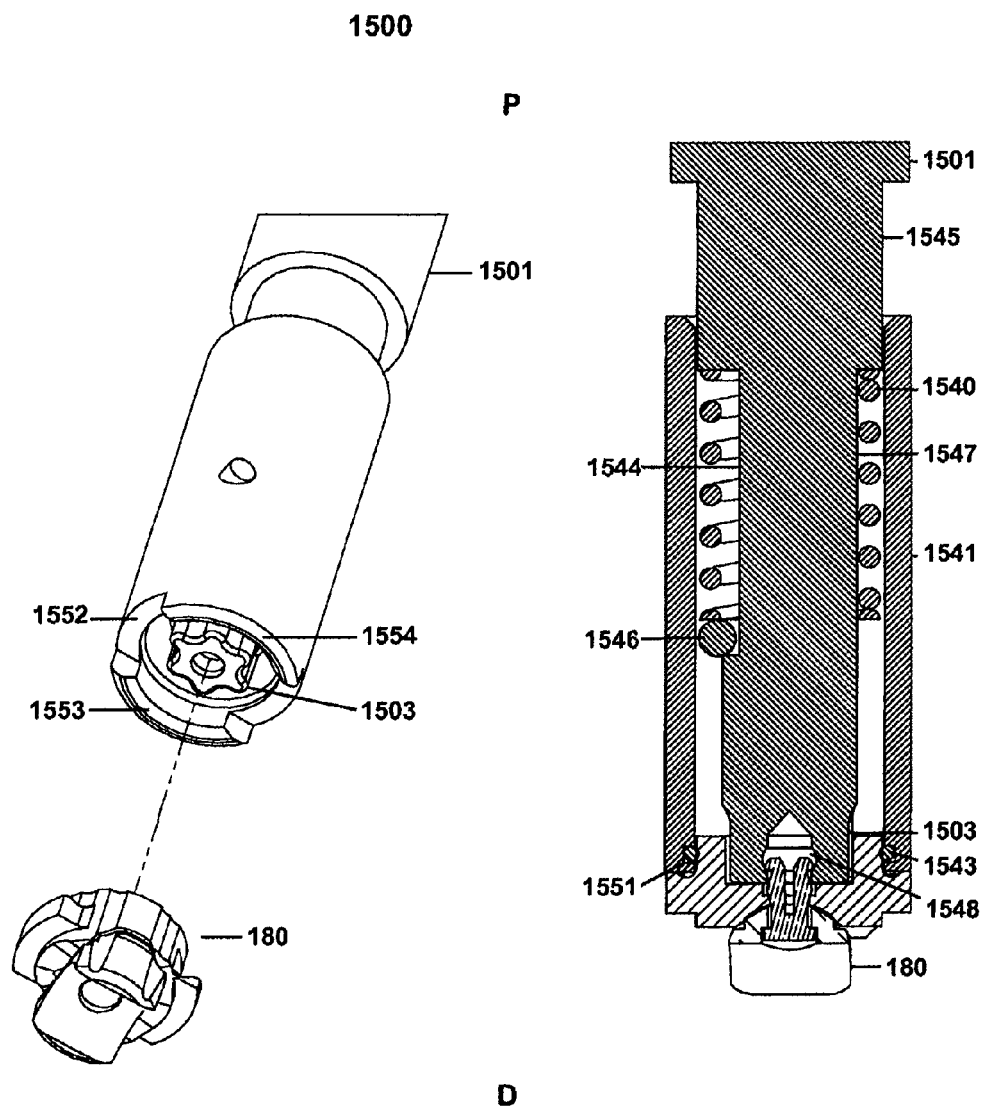
FIG. 22a is a perspective view of the sleeve of the drive rod of FIG. 21. with a locking device or cap.
FIG. 22b is a left side sectional view of the sleeve of the drive rod of FIG. 21. with the locking device or cap.

In yet another embodiment, the same "stab and grab" method is employed using the sleeve cap capture drive rod 1500 shown in FIGS. 21-22b. Like drive rods 1300 and 1400, drive rod 1500 performs the same function of reducing and locking a cap 180 in a coupling member. Sleeve capture drive rod 1500 has a distal end D and a proximal end P. Sleeve capture drive rod 1500 has a body 1501 with a diameter, depending distally from body 1501 is a smaller diameter portion 1545 creating sleeve abutment ledge 1549. Depending distally from smaller diameter portion 1545 is smallest diameter portion 1547 creating spring abutment ledge 1550. Drive surface 1503 depends distally from smallest diameter portion 1545.

Drive rod 1500 has a sleeve 1541 with a groove 1551 adjacent distal end D housing o-ring 1543 for the purpose of frictionally engaging the external wall 182 of a locking device 180. Sleeve 1541 has an outer diameter that matches that of body 1501 and an inner diameter that is slightly larger than smaller diameter portion 1545. Distal end D of sleeve 1541 has diametrically opposed slots 1552 that defines arms 1553, 1554. In use inside of arms 1553, 1554 contact outer wall 182 between flanges 185, 186 of locking device 180. Sleeve 1541 houses spring 1540 which surrounds smallest diameter portion 1547 with proximal end of spring 1540 abutting spring abutment ledge 1550. Spring 1540 is held within sleeve 1541 by the presence of alignment pin 1546 press fit in hole 1542 of sleeve 1541. Alignment pin 1546 performs two functions. Pin 1546 prevents the spring 1550 from advancing distally and also aligns the sleeve 1541 so that arms 1553, 1554 fit between flanges 185, 186 of locking device 180 and inner portion of arms 1553, 1554 contact outer wall 182. The pin 1546 press fit to sleeve 1541 rides on flat 1544 thus preventing sleeve 1541 from rotating about smallest diameter portion 1547.

Drive rod 1500 captures the locking device 180 in two ways. Contact of o-ring 1543 friction fitting with outer wall 182 of locking device previously described, and a pin 187 capturing groove 1548 inside a bore at distal end of drive surface 1503. As the cap 180 is pressed onto the drive surface splaying arms 188, 189 of pin 187 are urged toward one another until proximal portion of arms 188, 189 come to rest in groove 1548 thus releasably mating the drive rod 1500 to cap 180.

In use, the locking device or cap 180 is mated to the drive surface 1503 of drive rod 1500 in the orientation allowed by relationship of flanges 188, 189 and arms 1553, 1554. The cap 180 is temporarily held in place on drive rod 1500 by o-ring 1543 contacting outer wall 182, and proximal end of arms 188, 189 residing in groove 1548. During the procedure of locking the cap 180 to the coupling member 140 the distal ends of arms 1553, 1554 engage the proximal end of coupling member 140. The outer diameter of the sleeve 1541 is greater than the inside diameter of coupling member 140. As the drive rod 1500 is advanced distally the distal outside diameter portion of sleeve 1541 contacts the proximal end of the coupling member. As drive rod 1500 continues to be advanced distally, the pin 1546 in sleeve 1541 acts against spring 1540 thus keeping the sleeve 1541 stationary abutting proximal end of coupling member 140. As drive rod 1500 is advanced with cap 180, sleeve 1541 remains stationary, the cap 180 is driven past the friction fit of o-ring 1543, but remains attached at pin 187. Drive rod 1500 continues to be advanced until the connecting member or rod 160 is fully seated in u-shaped channel 144 of coupling member 140. The drive rod 1500 is initially rotated fifty degrees to partially lock the cap 180 in coupling member 160 and eventually to one hundred degrees to final lock the screw assembly 100. As the cap 180 is rotated the saddle portion 183 is advanced distally taking with it pin 187 thus pulling pin arms 188, 189 out of groove 1548 freeing drive rod 1500 from cap 180.

Figure 23:
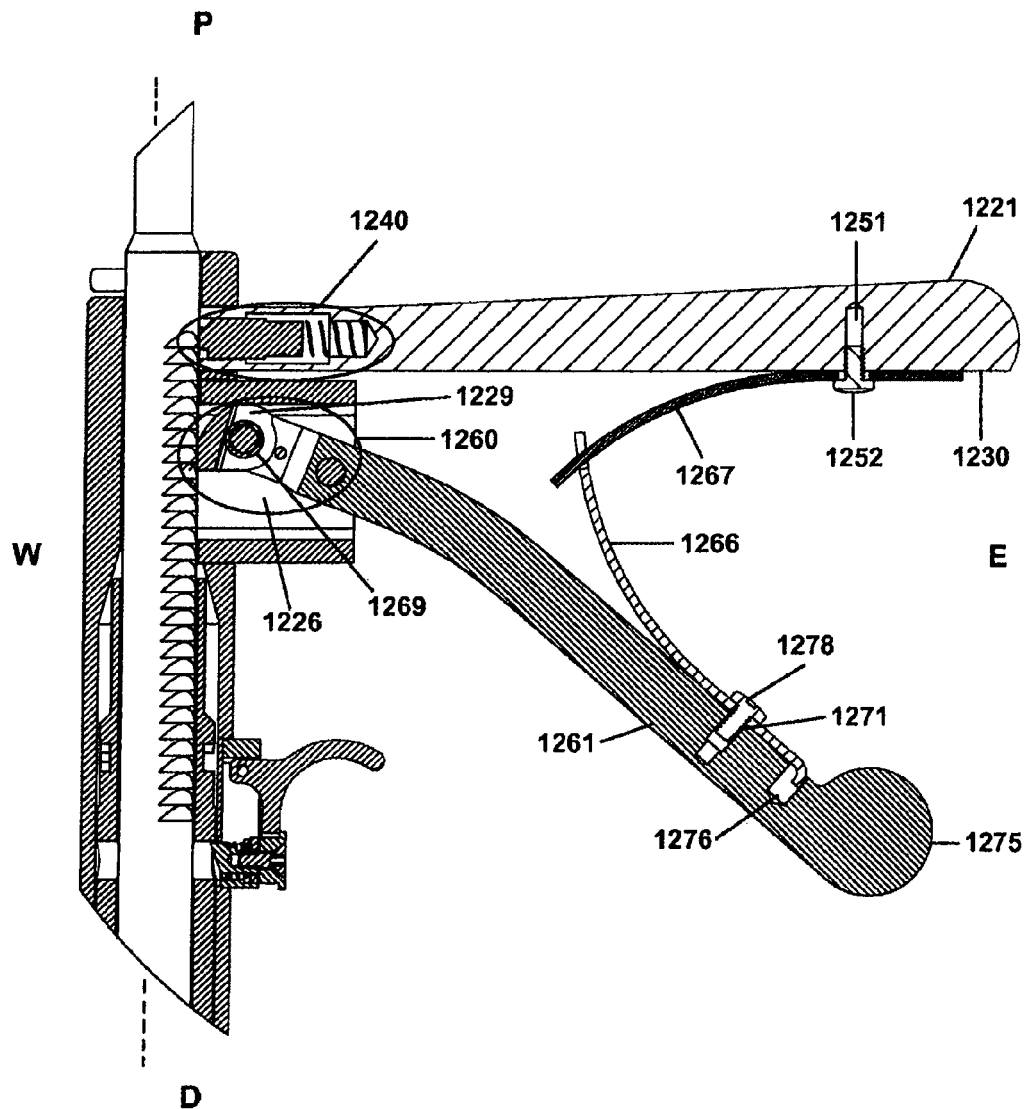
FIG. 23 is a front side sectional view of the proximal end of the drive tool with the drive rod.
Figure 24:
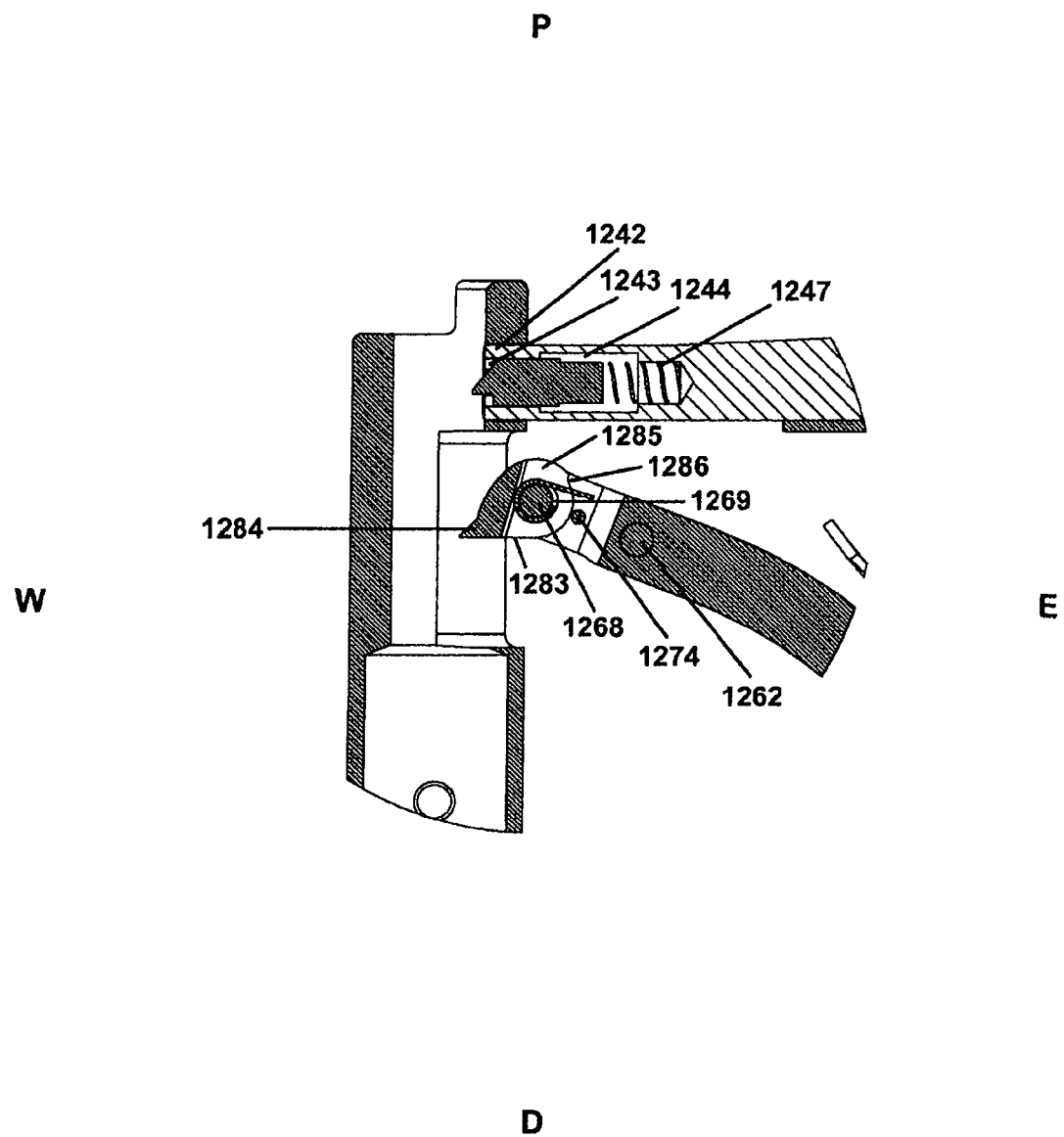
FIG. 24 is a front side sectional view of the mechanical engagement portion and the stop portion of the drive tool.

Turning now to FIGS. 23 and 24 and the interaction between the preferred drive tool 1200 and the unitary drive rod 1300. There are two elements that give the drive tool 1200 the ability to safely impart mechanical force and receive continuous tactile feedback on the drive rod 1300, mechanical linkage portion 1260 housed in mechanical linkage support portion 1226 and stop portion 1240 housed in stationary grip 1221. Drive tool 1200 has a distal end D and proximal end P and a longitudinal axis L as well as two transverse directions E and W. Both the mechanical linkage portion 1260 and stop portion 1240 function by pawls contacting drive portion 1302 of unitary drive rod member 1300.

Figures 25A, 25B:
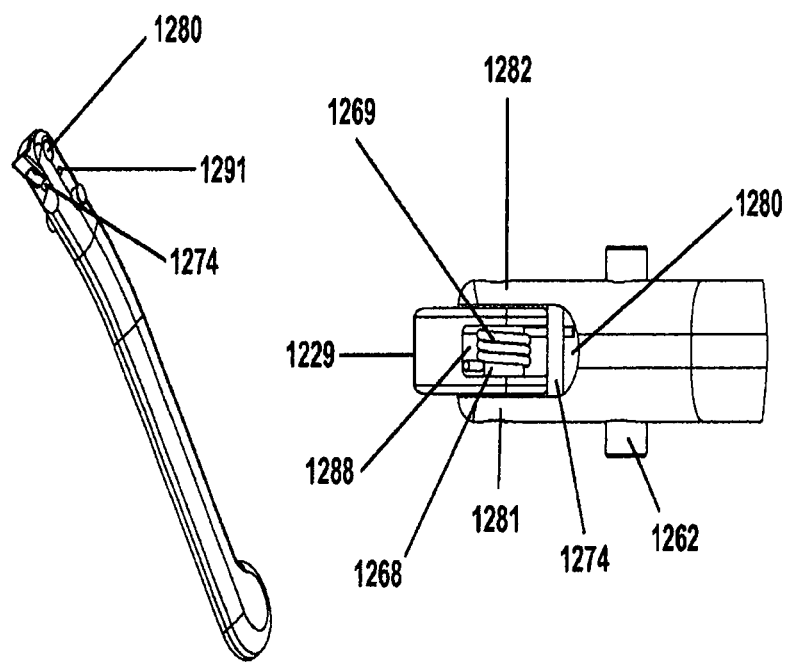
FIG. 25a is a perspective view of the actuating lever of the drive tool.
FIG. 25b is a top view of the actuating lever and pawl mechanism.
Figures 25C, 25D:
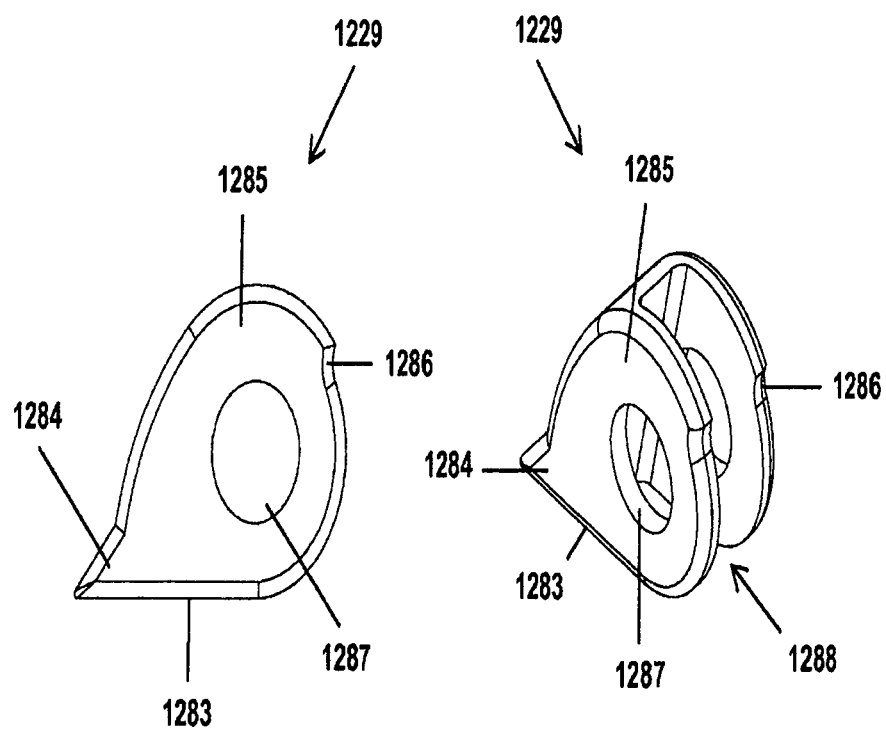
FIG. 25c is a front side view of the drive pawl mechanism.
FIG. 25d is a perspective view of the drive pawl mechanism.

The mechanical linkage portion 1260 includes drive actuator pawl 1229, torsion spring 1269, pawl pin 1268, stop pin 1274 and a fulcrum pin 1262 all captured in lever 1261. Lever 1261 is substantially rectangular in cross section, and is substantially straight with a slight bend adjacent proximal end as seen in FIG. 25. Lever 1261 has a semicircular distal end 1275 that prevents lever from traveling far enough to do damage to lever leaf spring 1266 and reduces possible pinch points. Depending from distal end 1275, lever has a bore 1276 partially through lever 1261 to receive end of leaf spring 1266 preventing the spring 1266 from moving in a lateral direction. Adjacent and proximal bore 1276 is a threaded bore 1277 for receiving lever leaf spring attachment screw 1278. Proximal the slight bend in the lever 1261 is fulcrum pin 1262. Adjacent and proximal to fulcrum pin 1262 is u-shaped slot 1280 defining arms 1281 and 1282 which house pawl 1229, pawl pin 1268, torsion spring 1269 and stop pin 1274.

Drive actuator pawl 1229, in the working position, has a flat 1283 on the distal end, a triangular portion 1284 in direction W, a substantially circular portion 1285 and a slight recessed portion 1286 forming a catch. Drive pawl 1229 has a bore 1287 in the center of the substantially circular portion 1285 to receive pawl pin 1268. Pawl also has a slot 1288 to accommodate spring 1269. In assembly, spring 1269 is placed in slot 1288 of pawl 1229 and both are placed in u-shaped slot 1280 in lever 1261. Pawl pin is then inserted through bore 1290 in lever 1261, into bore 1287 of pawl, through spring 1269 and out of the pawl hole 1287 and lever fulcrum pin hole 1290. Stop pin 1274 is then placed in the stop pin bore 1291, both ends being flush with the side of lever 1261. The bores of pawl 1229, spring 1269 (with stop pin 1274 in place) are lined up with fulcrum pin hole 1279 and fulcrum pin 1262 is inserted. Fulcrum pin 1262 is inserted through lever fulcrum pin hole 1279 capturing the pawl 1229 assembly and pin hole in mechanical linkage support structure 1225. Fulcrum pin 1262 is then secured to mechanical linkage portion support 1226 by laser welding or by any other means known in the art.

Figure 10B:
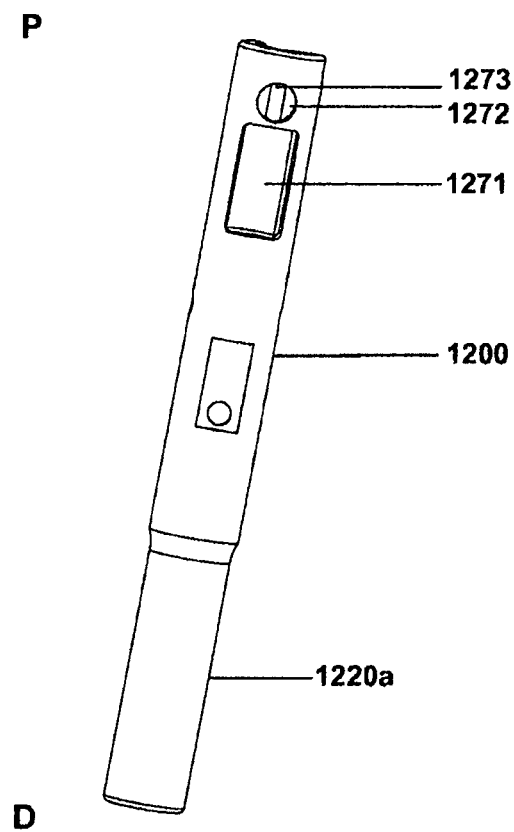
FIG. 10b is a right side view of an elongate body of the drive tool.
Figure 11:
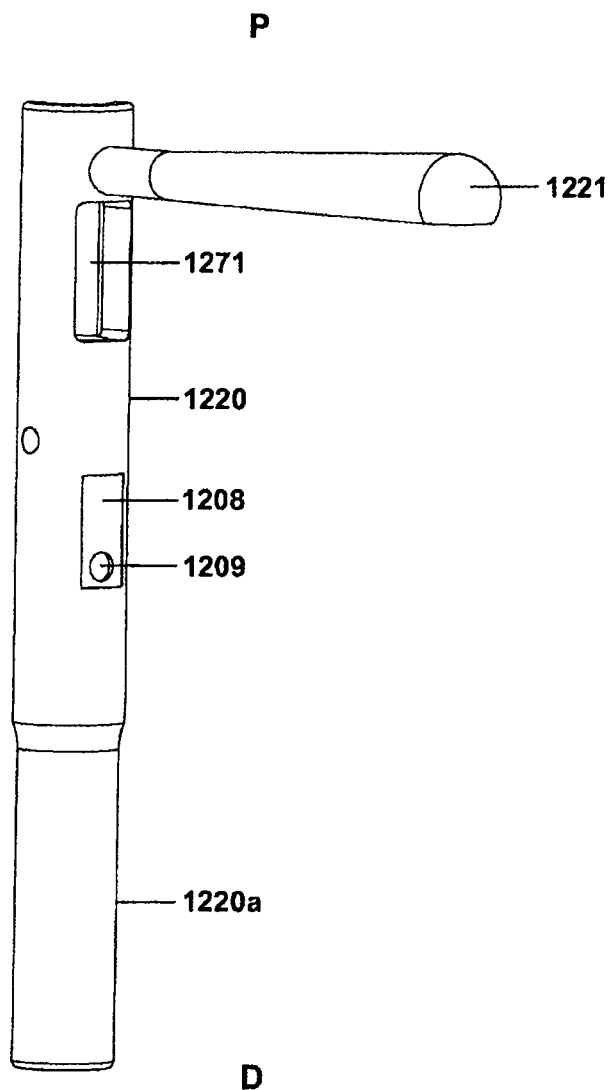
FIG. 11 is a perspective view of the drive tool elongate body with a stationary grip.

Referring now to FIGS. 24-27, the stationary grip 1221 performs two functions, it serves as a stationary handle for the operator to hold while squeezing lever 1261, and it houses stop portion 1240 which in operation prevents drive rod 1300 from releasing or otherwise receding proximally while drive rod 1300 is reducing connecting member 160. The stationary grip 1221 is located adjacent proximal end of drive tool 1200 and extends transverse and preferably substantially orthogonal to the longitudinal axis of drive tool 1200. Stationary grip 1221 is attached to drive tool 1200 at bore 1272 abutting slot 1273 as seen in FIGS. 10b and 13. Stationary grip in cross section is semicircular with a flat 1230 in the distal direction and is tapered with a wider end in direction E leading to a narrower end in direction W. Flat 1230 ends adjacent drive tool 1200 leaving stationary grip fully circular in cross section 1255 at the end to be inserted in bore 1272. Stationary grip flat 1230 has a threaded bore hole 1251 to receive screw 1252 to secure stationary grip leaf spring 1267. Stationary grip 1221 is solid except at end 1242 disposed in drive tool 1200. End 1242 consists of a hexagonal bore 1243, large circular bore 1244 which houses stop pawl 1246, and smaller circular bore 1245 which houses stop pawl spring 1247. Stop pawl 1246 has circular end 1248 which engages spring 1247, hexagonal portion 1249 which mates with hexagonal bore 1243, and substantially triangular shape drive surface engagement end 1250 which resides in slot 1273 of elongate body 1220 of drive tool 1200.

In assembly, spring 1247 is placed in small circular bore 1245, stop pawl 1246 is placed in hexagonal bore 1243 of grip 1221 which in turn is then placed in bore 1272 of drive tool 1200 such that stationary grip flat 1230 is facing distal direction D on drive tool 1200. The grip 1221 is then press fit, welded or otherwise attached to body 1220. Hexagonal bore 1243 is slightly larger than hexagonal portion 1249 on stop pawl 1246 allowing stop pawl 1246 to slide back and forth in hexagonal bore 1243 while not allowing stop pawl 1246 to rotate. Slot 1273 is slightly wider than drive surface engagement end 1250 but not wider than hexagonal portion 1249 thus allowing surface engagement end 1250 to enter the shaft of elongate body 1220 while restraining the entire stop pawl 1246 from doing so. Stop pawl spring 1247 urges stop pawl 1246 toward the shaft of drive rod elongate body 1220 while allowing it to completely recede in hexagonal and circular bores 1243,1244 should there be enough force against pawl 1246 to collapse spring 1247.

Once the pedicle screw assemblies 100 attached to yoke manipulators 1100 are deposited in the vertebral bodies and rest on the pedicles, the connecting member 160 is introduced and delivered so that it rests just above and spans both of the coupling members 140. It is at this point that rod 160 needs to be reduced into the coupling members 140 and locked in place with locking device or cap 180.

Figure 29:
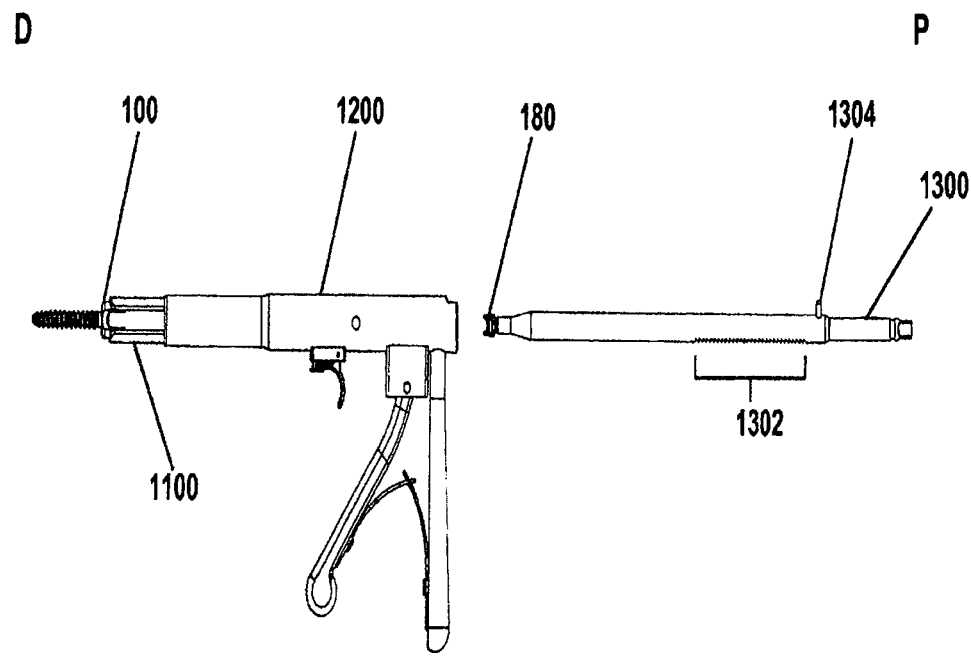
FIG. 29 is a front side view of the drive rod in the proper orientation to enter the drive tool so that drive surface engages both the drive pawl and the stop pawl, and the alignment pin abuts the zero degree wall.
Figure 30:
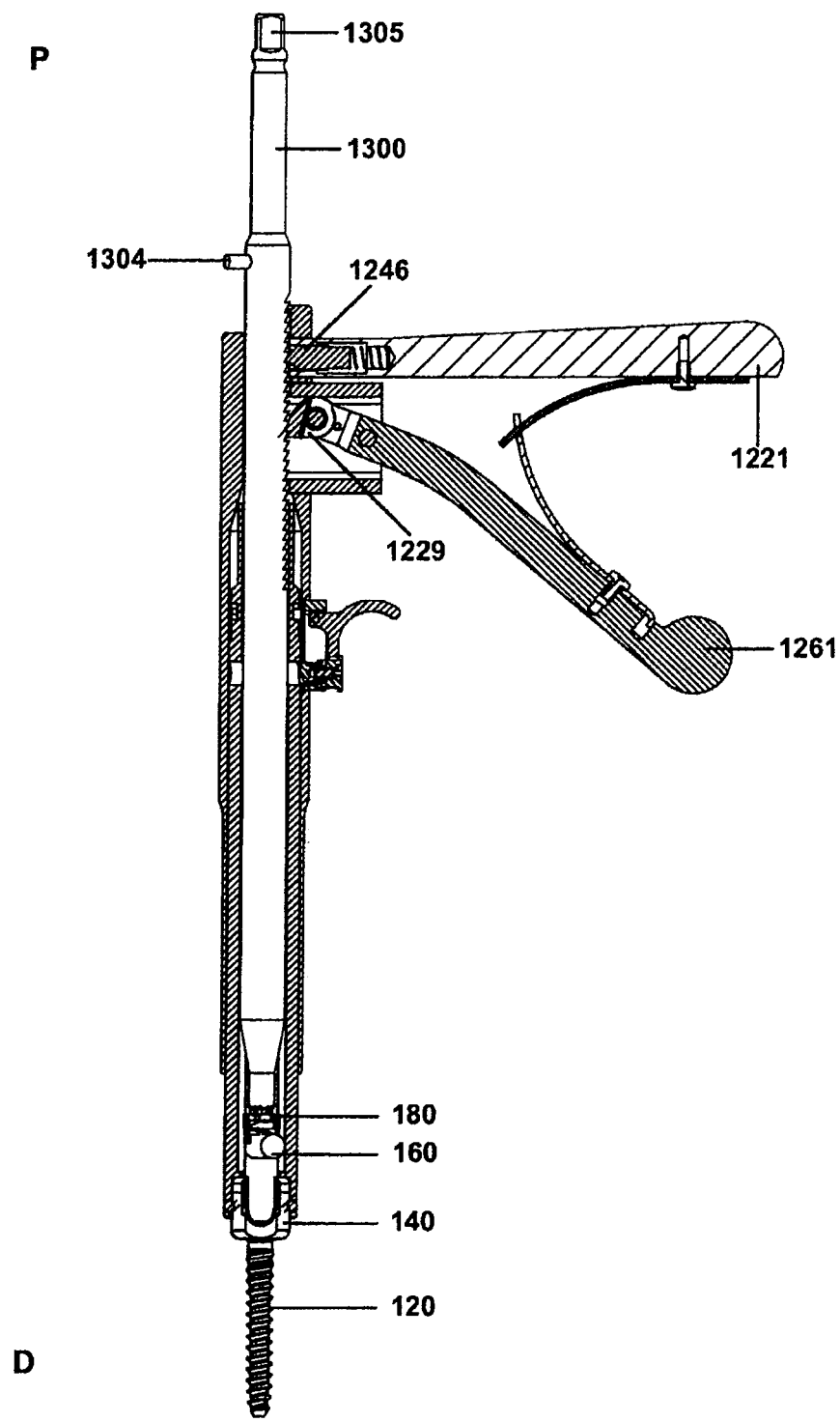
FIG. 30 is a front side sectional view of the drive rod in the entry orientation with the drive portion engaging both the drive pawl and the stop pawl.

Drive tool 1200 is attached to yoke manipulator 1100 with attachment mechanism 1201 as previously described. Cap 180 is placed on drive rod 1300 with the "stab and grab" technique. The operator grasps the tool holding stationary grip 1221 and actuating lever 1261. Drive rod 1300 with cap 180 attached to distal end are introduced into shaft of drive tool 1200 from the proximal end thereof and eventually into yoke manipulator 1100 disposed in drive tool 1200, in an orientation such that drive portion 1302 will contact both stop pawl 1246 and drive pawl 1229 as seen in FIG. 29. This orientation will be visual with alignment pin 1304 which will ultimately reside against zero degree wall 1231 of mechanical guide portion 1223 once rod 160 and locking device 180 are fully reduced in coupling member 140 as seen in FIG. 28a. The drive rod 1300 and cap 180 can be advanced manually proximally down the shaft toward the surgical site. Once drive portion 1302 of drive rod 1300 comes in contact with stop pawl 1246 an audible clicking noise will be heard letting the operator of drive tool 1200 hear and feel that the drive rod 1300 is in engagement with the stop pawl 1246. With drive portion 1302 of drive rod 1300 in engagement with stop pawl 1246, the operator can continue with manual advancement or take advantage of the mechanical advancement provided by squeezing lever 1261 proximally toward stationary grip 1221.

When the operator of the drive tool 1200 decides to employ mechanical advancement of drive rod 1300, the operator uses the tool's handle assembly. In the illustrated and preferred form, the handle assembly includes stationary grip 1221 and actuating lever 1261 with the operator grasping stationary grip 1221 and the activating lever 1261 in one hand and pulling activating lever 1261 proximally toward the grip 1221. As the activating lever 1261 is pulled toward the grip 1221 it pivots about fulcrum pin 1262, thereby moving the drive pawl 1284 distally. Since the drive pawl 1284 is engaged against flat 1310 and angle portion 1311 of the ratchet teeth of drive portion 1302 of drive rod 1300, the distal motion of the drive pawl 1284 drives the drive rod 1300 distally. Also depicted in these views is stop pawl 1246 and a stop pawl spring 1247. Stop pawl 1246 cannot move distally or proximally, but the stop pawl spring 1247 allows stop pawl to move away from the drive rod 1300 as each angled ratchet tooth advances distally. Once each tooth passes stop pawl 1246, pawl spring 1247 pushes stop pawl 1246 back toward driving rod 1300, to engage the next ratchet tooth along drive portion 1302 of drive rod 1300. Thus the stop pawl 1246 allows distal motion of drive rod 1300 but prohibits proximal motion of drive rod 1300. In this regard, the tool 120 has a one-way locking mechanism by allowing the drive rod 1300 to be advanced and blocking the drive rod 1300 against being forced back upward in the shaft assembly 1220. As activating lever 1261 is pulled again or nearer toward the stationary grip 1221, further distal motion is imparted to drive rod 1300.

Thus, stop pawl 1246 and stop pawl spring 1247 cooperate to restrict or oppose proximal motion of drive rod 1300 as the activating lever 1261 is released by the operator. In the depicted embodiment, actuating lever 1261 is biased away from stationary grip 1221 by leaf springs 1266, 1267 toward its initial position. As this occurs, torsion spring 1269 allows drive pawl 1284 to move proximally along drive portion 1302 of drive rod 1300. This occurs with no distal or proximal motion of drive rod 1300 since torsion spring 1269 allows drive pawl 1284 to move away and toward drive rod 1300 along the ratchet teeth of drive rod 1300 as drive pawl 1284 ramps along drive portion 1302 proximally. The stop pawl 1246, engaged against the ratchet teeth of drive portion 1302, opposes proximal motion of drive rod 1300 during this action. It should be noted, that the actuating lever 1261 need not be abutting stationary grip 1221 to be released, but that actuating lever 1261 may be released at any time the operator sees fit. It is during the course of squeezing the lever that the operator of drive tool 1200 gets immediate tactile feedback of the resistance that rod 160 is encountering with tissue surrounding pedicle screw assembly 100. It is contemplated that alternative types of driving mechanisms could be employed with stop pawl 1246 and stop pawl spring 1247. Pawl 1246 and spring 1247 could be used to provide similar restricted proximal motion of a drive rod where the drive rod 1300 comprises some ratchet teeth on at least a portion of the drive rod 1300 which can cooperate with stop pawl 1246 and stop pawl spring 1247. An example would be a toothless ratchet relying on friction.

Figure 31:
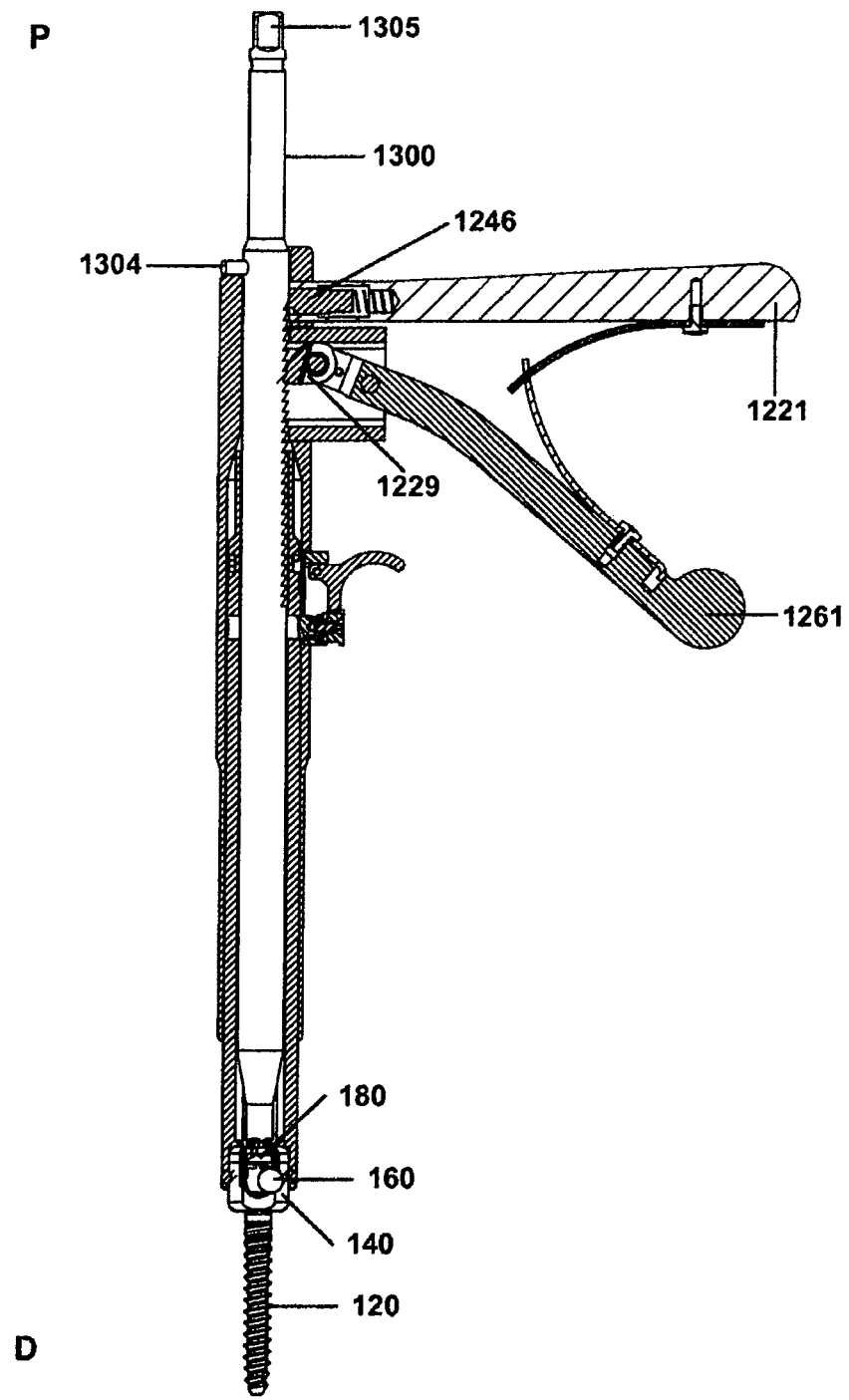
FIG. 31 is a front side sectional view of the drive rod fully deployed in the drive tool and the locking device and connoting member seated in the coupling member with the alignment pin abutting the zero degree wall (not seen)
Figure 32:
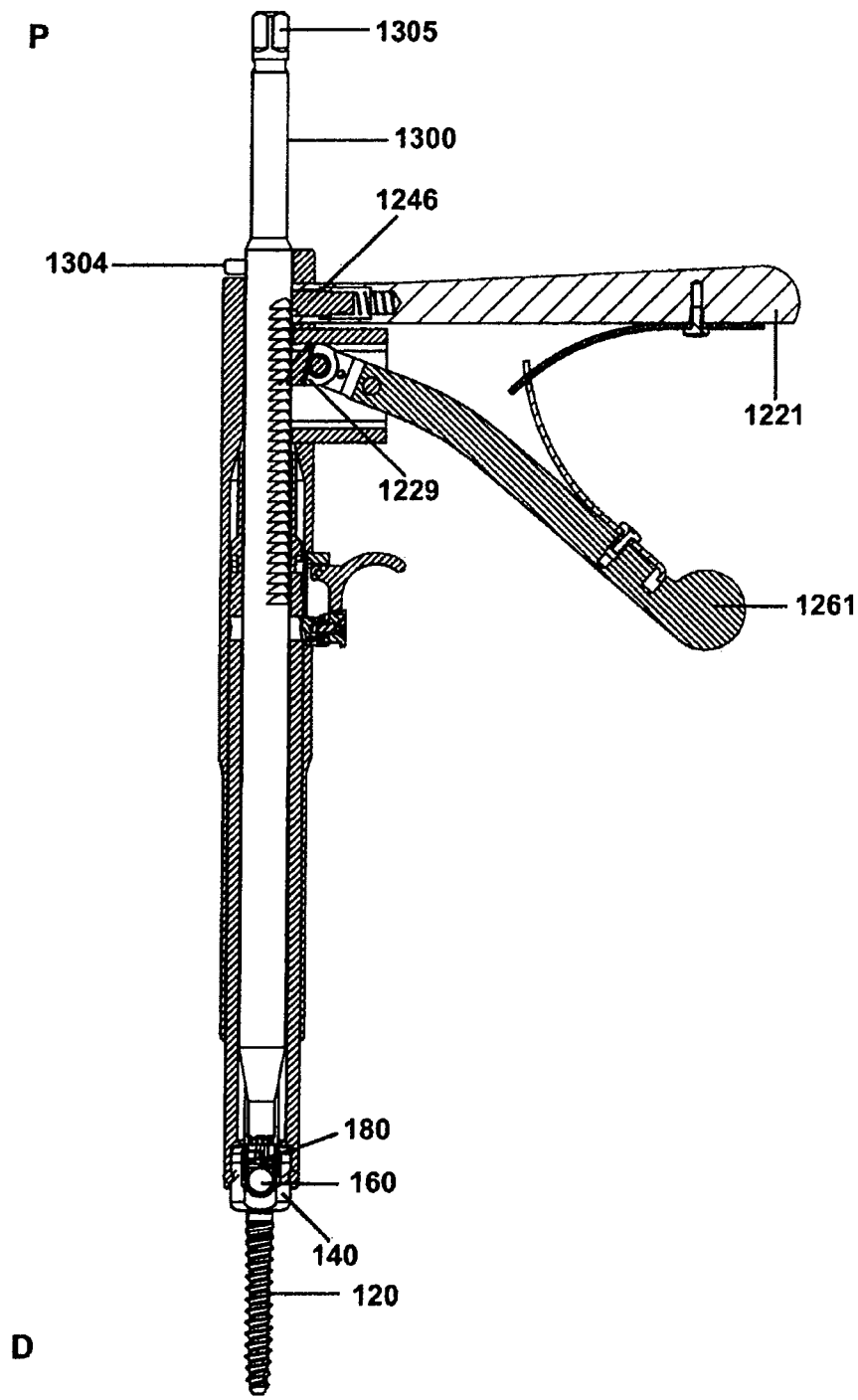
FIG. 32 is a front side sectional view of the drive rod fully deployed in the drive tool and the locking device and connoting member seated in the coupling member with the alignment pin abutting in the 40-50 degree position with the drive portion still engaged to drive pawl and stop pawl.

The present invention provides a method for reducing, and rotating a spinal rod 160 as well as the compression or distraction of vertebrae. For the sake of simplicity, a one level surgery is considered with two pedicle screw assemblies 100 and a single connecting member or rod 160. Once the connecting member 160 and cap 180 have been successfully reduced and seated in the coupling member 140 alignment pin 1304 of drive rod 1300 should be abutting zero degree wall 1231 as seen in and flat 1222 of mechanical guide portion 1223 on body 1220 of guide tool 1200 as shown in FIGS. 28*a* and 31. By turning drive rod 1300 in a clockwise direction so that alignment pin 1304 lies roughly half way between zero degree wall 1231 and hard stop 1224 of mechanical guide portion 1223 the rod 160 is captured in the coupling member 140 by locking device 180 as shown in FIGS. 28*b* and 32. The resulting temporary lock relieves all the pressure once on drive rod 1300 transferring it to cap 180. At this point rod 160 and coupling members may still be manipulated. This rotation also causes the pawls 1246 and 1284 to disengage from the drive teeth of the drive rod 1300.

Figure 33:
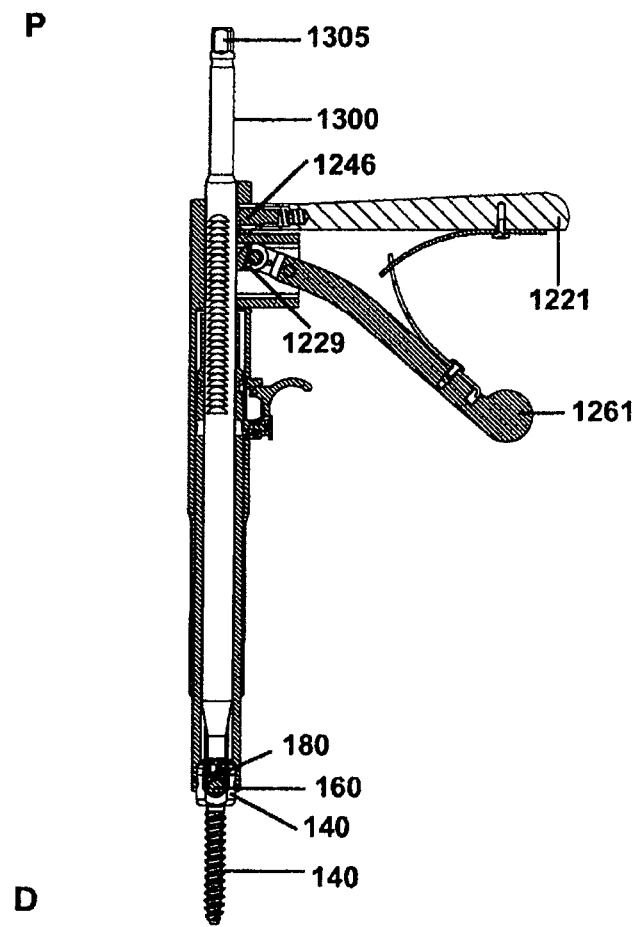
FIG. 33 is a front side sectional view of the drive rod fully deployed in the drive tool and the locking device and connecting member seated in the coupling member with alignment pin (now not seen) abutting the hard stop wall with the drive portion no longer engaged to drive pawl and stop pawl.

In the case of the need for spinal compression or distraction, the physician temporarily locks both of the caps 180 in coupling members 140 thereby capturing the rod 160. The physician then elects one of the assemblies 100 to put in a final lock position. The temporary lock on the one assembly 100 will still allow for movement relative to the rod 160. The physician then can either distract or compress the vertebrae depending on the type of surgery that is being performed. Once the vertebrae are a desired distance from one another, the surgeon then puts the last assembly 100 in a final lock. Final lock is achieved by rotating drive rod 1300 until alignment pin 1304 abuts hard stop wall 1224 on drive tool 1200 as seen in FIGS. 28*c* and 33.

In the case of spinal deformity rod rotation is often necessary. In a typical surgery where rod rotation is not necessary, the drive tools 1200 when inserted will extend from the patients body substantially perpendicular to the longitudinal axis of the spine. In surgeries that require rod rotation the drive tools often will come reside at a variety of angles off the spine. With the locking devices 180 in both coupling members 140 temporarily locked, the surgeon, manipulates the first drive tool 1200 so that is in the physician desired position roughly perpendicular to the longitudinal axis of the spine. Once the drive tool is in position the surgeon rotates the drive rod 1300 to the final lock position where alignment pin 1304 abuts hard stop 1224. In the final lock position the drive rod 1300 has been rotated approximately one hundred degrees which is enough to free drive portion 1302 from contact with both drive pawl 1229 and stop pawl 1246. The drive rod 1300 can then be manually removed from shaft of drive tool 1200. The second drive tool 1200, if necessary, is moved into physician desired position and final locked. In cases of severe scoliosis and open surgery may be necessary, despite the fact that the drive tool 1200 and manipulator 1100 were designed for MIS surgeries it is contemplated that both could be used in an open technique without modification.

The tools 1200, 1100 and 1300 as well as implant devices 100, 140, 160 and 180 can be made from any suitable, structurally strong material. The structural portions and other components are constructed of suitable materials which are compatible with the uses and environments into which the apparatus will be utilized. Preferably, the tools and implants principally are constructed of metallic materials such as 17-4 stainless steel, or titanium, but not limited to those materials. The tools as well as implant devices are made using standard lathes, milling machines, electro discharge machining as well as T-IG and laser welding. Alternatively, other standard manufacturing processes such as casting could be used.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for driving a spinal rod down into a coupling of a spinal screw assembly and locking the rod securely with a locking device of the spinal screw assembly, the apparatus comprising:
    an elongate shaft assembly having a longitudinal bore, upper and lower ends, and a longitudinal axis extending therebetween;
    an elongate drive rod of unitary construction sized to fit in the longitudinal bore;
    a lower portion of the unitary drive rod having a distal end configured for receiving the locking device of the spinal screw assembly;
    an upper portion of the unitary drive rod including a proximal end for projecting beyond the upper end of the shaft assembly; and
    an actuating mechanism configured to cooperate with the drive rod upper portion so that operation of the actuating mechanism drives the unitary drive rod including both the upper and lower portions thereof linearly without rotation down along the longitudinal axis in the bore of the shaft assembly for driving the spinal rod down into the spinal screw assembly coupling then allowing the unitary drive rod including both the upper and lower portions thereof to both be rotated in the shaft assembly bore via rotation of the proximal end of the drive rod for locking the spinal rod in the coupling with the locking device that is received by the distal end of the drive rod lower portion,
    wherein the actuating mechanism and drive rod upper portion have a drive interface therebetween including a drive portion of the drive rod upper portion and a drive portion of the actuator mechanism in engagement with each other for linear driving of the drive rod with the drive rod drive portion being disposed along one side of the drive rod upper portion so that rotating the drive rod causes the drive interface portions to disengage from each other.

2. The apparatus of claim 1 wherein the drive portion of the drive rod includes drive teeth formed along the drive rod, and the drive portion of the actuating mechanism comprises a drive pawl for being engaged with the drive teeth and a handle assembly connected to the drive pawl and being operable to cause the drive pawl to shift down toward the shaft assembly lower end for driving the drive rod downwardly.

3. The apparatus of claim 2 wherein the handle assembly includes a lower pivotal lever and an upper stationary grip with the handle assembly being operated by pivoting the lever toward the stationary grip.

4. The apparatus of claim 1 wherein the actuating mechanism includes a handle assembly having a pair of handles operatively mounted to the shaft assembly for being gripped and operated by a user for driving of the drive rod, and one of the handles having a one-way locking mechanism mounted thereto.

5. The apparatus of claim 1 wherein the shaft assembly has a releasable connector device for releasably connecting a shaft extender thereto that is sized and configured to extend beyond the lower end of the shaft assembly to attach to the spinal screw assembly coupling.

6. The apparatus of claim 1 wherein the elongate shaft assembly and the drive rod have an alignment mechanism which is configured to provide a visual indication that the drive rod upper portion is in rotary alignment with the actuating mechanism for driving of the drive rod by operation of the actuating mechanism.

7. The apparatus of claim 6 wherein the alignment mechanism is further configured to provide a visual indication that the locking device is fully locked in the coupling by rotation of the drive rod.

8. The apparatus of claim 1 wherein the actuating mechanism and drive rod upper portion are configured so that repeated operation of the actuating mechanism sequentially drives the unitary drive rod linearly without rotation farther down along the longitudinal axis in the bore of the shaft assembly.

9. A drive tool for driving a spinal rod, the drive tool comprising:
   an elongate body having a throughbore and proximal and distal ends;
   an elongate drive member configured to rotatably fit in the throughbore;
   a drive actuator mounted to the body operable to advance the drive member along the elongate body in the throughbore in a spinal rod driving direction toward the distal end thereof; and
   a lock device mounted to the body to keep the advanced drive member from returning back toward the proximal end of the elongate member after operation of the drive member,
   wherein the drive member has drive teeth along one side thereof, the drive actuator comprises a drive pawl in engagement with the drive teeth, and the lock device comprises a locking pawl biased into engagement with the drive teeth above the drive pawl and rotationally aligned therewith so that the locking pawl provides an audible indication that the drive member is oriented properly in the throughbore to have the drive teeth engaged with the drive pawl and the locking pawl.

10. The drive tool of claim 9 wherein the drive actuator includes a handle assembly mounted to the elongate body for being held and operated by a user to cause the drive member to be advanced in the driving direction.

11. The drive tool of claim 10 wherein the handle assembly includes a pivotal lever for being pivoted by a user for advancing the drive member in the driving direction.

12. The drive tool of claim 10 wherein the handle assembly includes a stationary grip member having the lock device mounted thereto.

13. The drive tool of claim 9 wherein the drive teeth are disposed along only one side of the drive member and the locking pawl is circumferentially aligned with the drive pawl about the drive member so that with the drive member received in the elongate body throughbore the drive teeth of the drive member are engaged with the drive pawl and the locking pawl.

* * * * *